United States Patent [19]

Parsons et al.

[11] Patent Number: 5,106,626
[45] Date of Patent: Apr. 21, 1992

[54] OSTEOGENIC FACTORS

[75] Inventors: Thomas F. Parsons, Arcadia; Arup Sen, Van Nuys; Lynn Grinna, Santa Monica, all of Calif.; Carol Hersh, Great Neck, N.Y.; Georgia Theofan, Los Angeles, Calif.

[73] Assignee: International Genetic Engineering, Inc., Santa Monica, Calif.

[21] Appl. No.: 415,555

[22] Filed: Oct. 4, 1989

Related U.S. Application Data

[63] Continuation-in-part of Ser. No. 256,034, Oct. 11, 1988, abandoned.

[51] Int. Cl.$^5$ .............. A61F 2/28; A61K 35/32; A61K 37/12; C07K 15/20
[52] U.S. Cl. ................. 424/423; 424/422; 424/484; 424/548; 424/549; 530/350; 530/353; 530/840; 623/16
[58] Field of Search ............ 530/350, 353, 840; 424/422, 423, 548, 549, 484; 623/16

[56] References Cited

FOREIGN PATENT DOCUMENTS

WO89/09787 10/1989 PCT Int'l Appl. .
WO89/09788 10/1989 PCT Int'l Appl. .

OTHER PUBLICATIONS

Wang et al., Proc. Natl. Acad. Sci. U.S.A., 85, pp. 9484–9488, Dec. 1988.

Primary Examiner—Thurman K. Page
Assistant Examiner—Carlos Azpuru
Attorney, Agent, or Firm—Marshall, O'Toole, Gerstein, Murray & Bicknell

[57] ABSTRACT

The present invention provides an osteogenically active protein preparation characterized by a molecular weight of from about 31,000 to 34,000 daltons as characterized comprising a subunit identical to or homologous to a subunit in P3 OF 31-34, by non-reducing sodium dodecyl sulfate polyacrylamide gel electrophoresis and by the characteristic of eluting from a reverse phase high performance liquid chromatography column equilibrated with buffers containing trifluoroacetic acid and acetonitrile by eluting within the concentrations of 35% to 45% acetonitrile. The invention further provides improved methods for isolating such preparations and genes encoding all or a portion of polypeptide subunits of dimers comprising the osteogenic protein preparation.

12 Claims, 26 Drawing Sheets

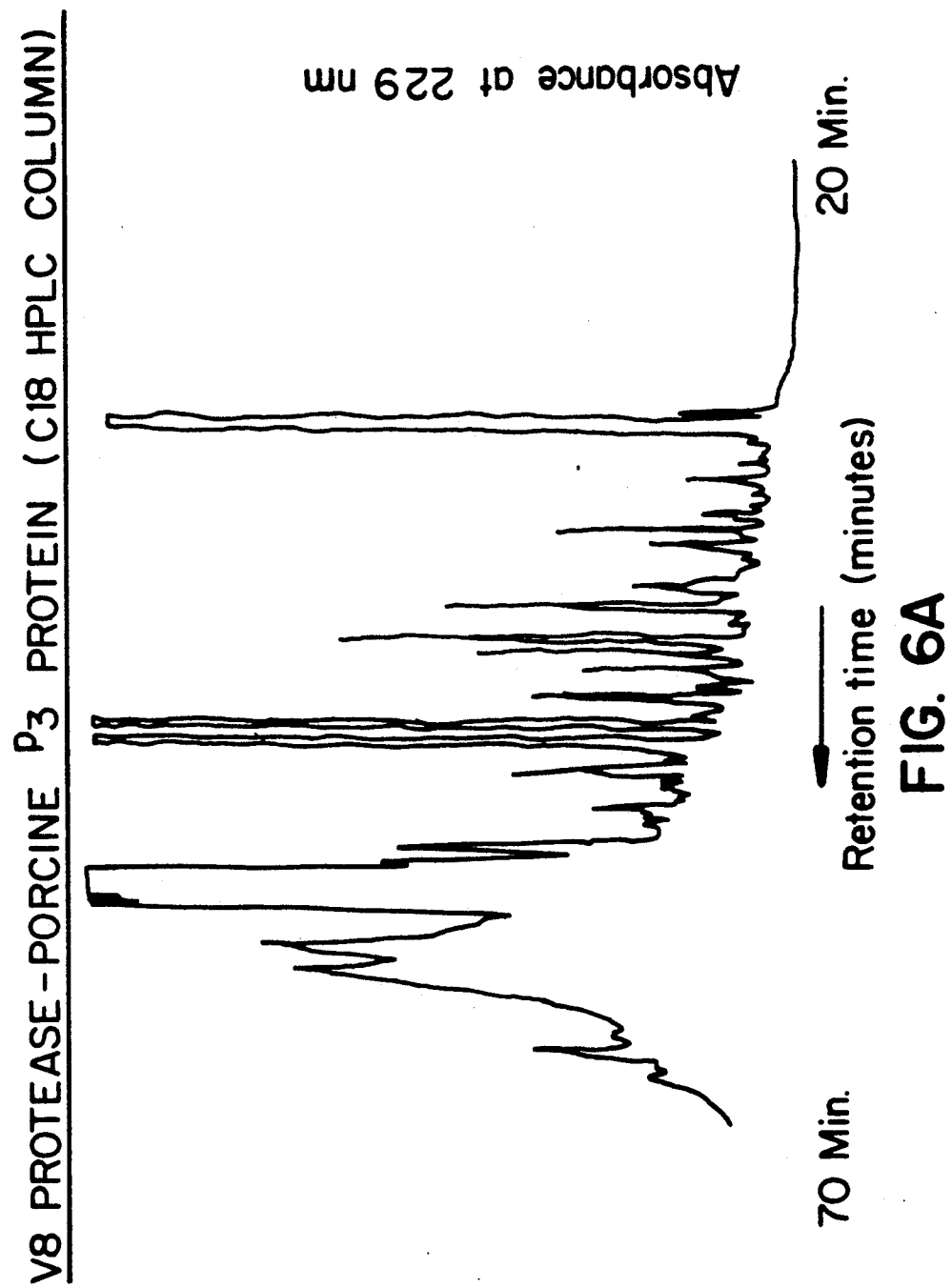

Purification of Osteogenic Factors

FIG. 9 cont.

G-25 Pool
│ Q-Sepharose Column
│ 6 M Urea
│ 20 mM Ethanolamine
↓
QS Pool
│ C-18 HPLC Column
│ 0.05% TFA
│ 35% through 45% Acetonitrile
│ Lyophilize
│ Reconstitute
↓
Prep HPLC Pool
│ $Cu^{2+}$ Chelating Sepharose Column
│ 6 M Urea
│ 50 mM Tris
│ 20 mM Ethanolamine
│ 0.5 M NaCl
↓
CC Pool
│ Phenyl-Sepharose Column
│ 25% Ammonium Sulfate
│ 6 M Urea
│ 50 mM Tris
↓
PS Pool
│ C-18 HPLC Column
│ 0.05% TFA
│ 35% through 45% Acetonitrile
↓

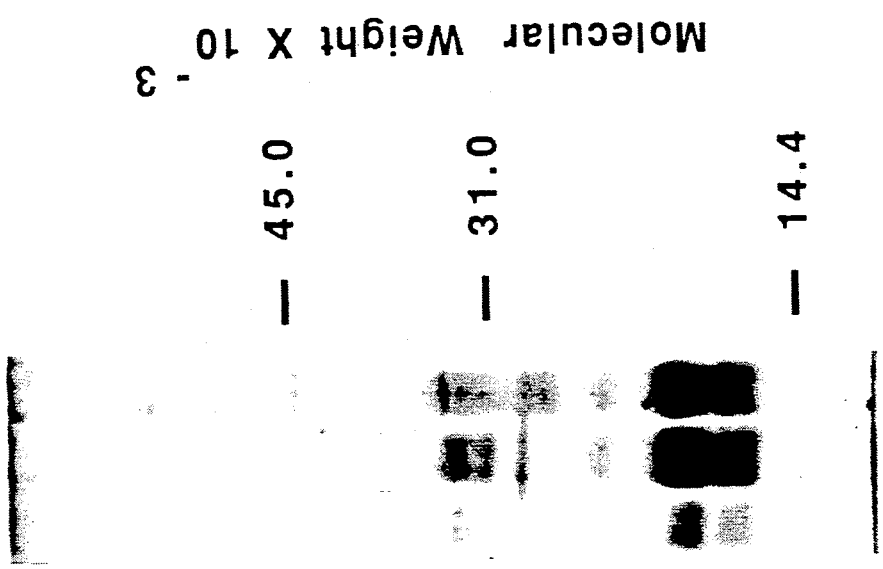
FIG.10B +DTT
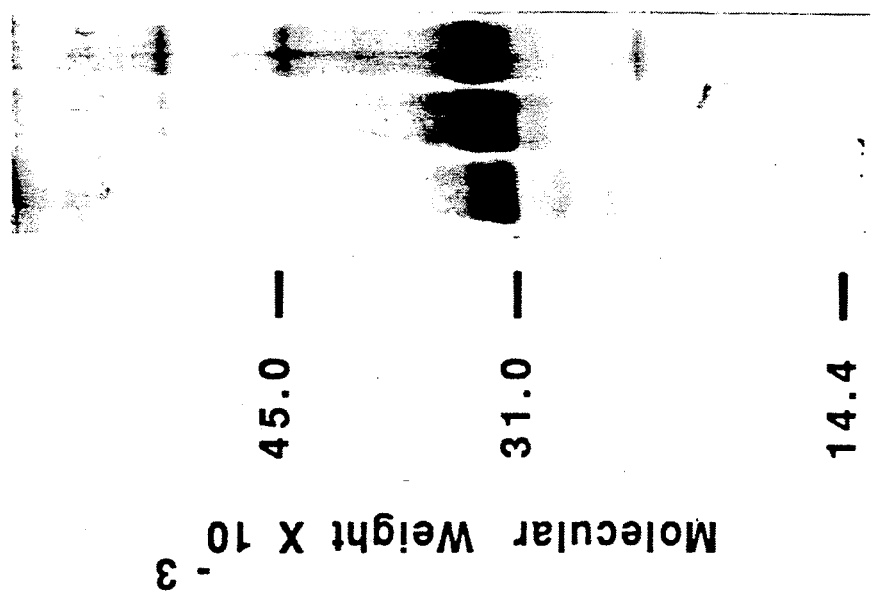
FIG.10A −DTT

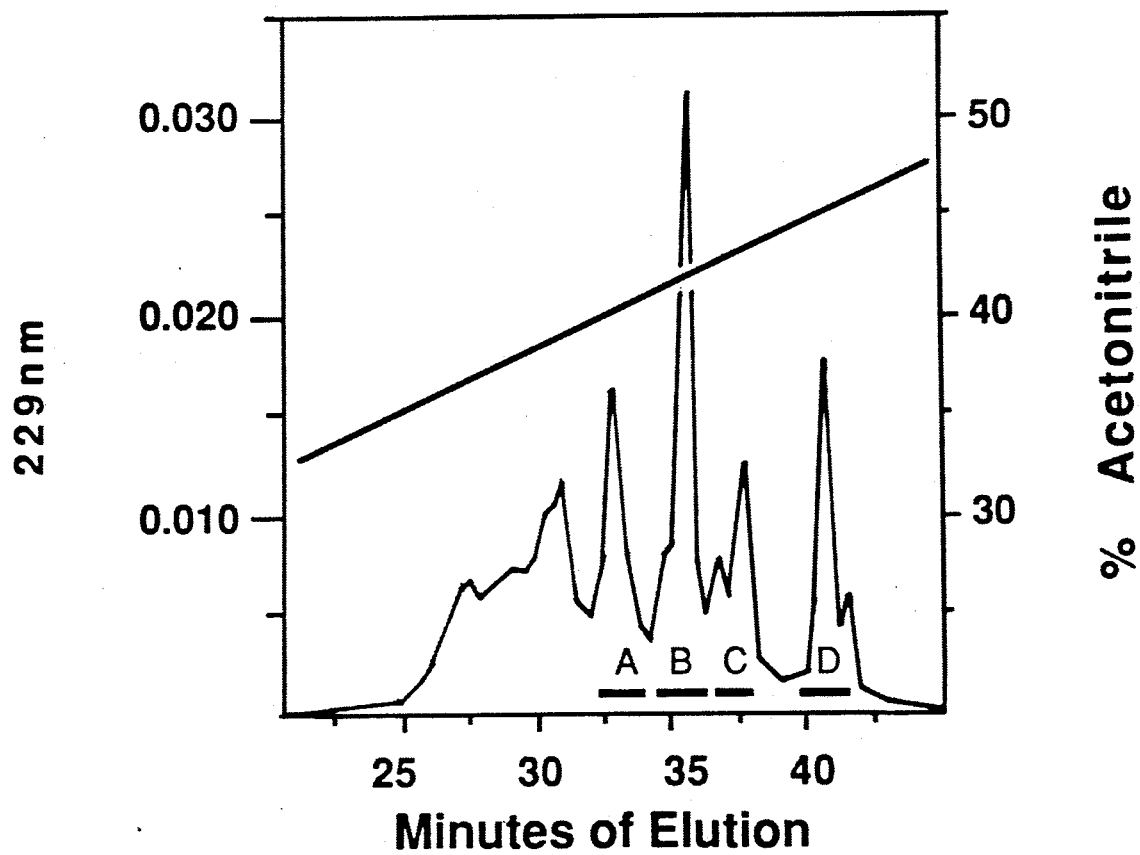
FIG.IIA
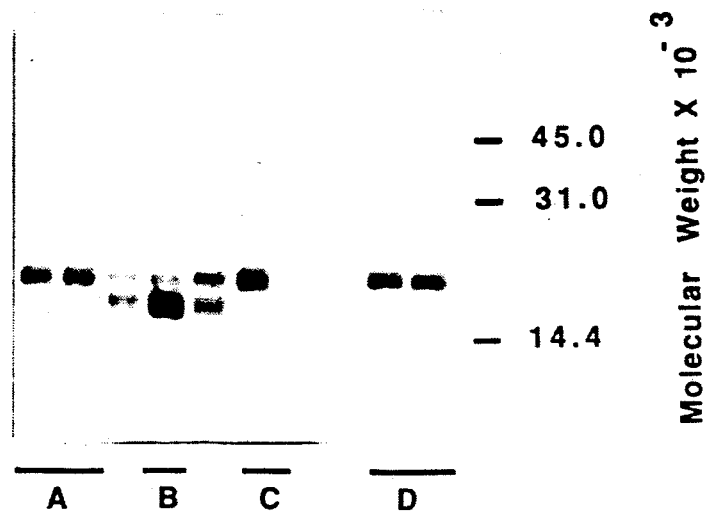
FIG.IIB

FIG.12

```
BMP-2A    Q A . . K H K . Q R K R L K S S . . . . . . . . . . . . . .
BMP-2B    S P . . K H H S Q R A R K K N K N . . . . . . . . . . . . .
Vgr-1     S A S S R R R Q Q S R N R S T Q S Q D V S R G S G S S D Y

A      S A P G R R R Q Q A R N R S T P A Q D V
   B
   C      S x . . K H x x Q R x R K K N N
   D      S T G G K Q R S Q N R S K T P K N Q E A
  hOD                         S K T P K N Q E A L R M A N V A E N
  hOE                         N K S S S H Q D S S R M S S V G D Y

BMP-2A    . . . . . . . . C K R H P L Y V D F S D V G W N D W I V A
BMP-2B    . . . . . . . . C R R H S L Y V D F S D V G W N D W I V A
Vgr-1     N G S E L K T A C K K H E L Y V S F Q D L G W Q D W I I A

A
   B
   C
   D
  hOD     S S S D Q R Q A C K K H E L Y V S F R D L G W Q D W I I A
  hOE     N T S E Q K Q A C K K H E L Y V S F R D L G W Q D W I I A

BMP-2A    P P G Y H A F Y C H G E C P F P L A D H L N S T N H A I V
BMP-2B    P P G Y Q A F Y C H G D C P F P L A D H L N S T N H A I V
Vgr-1     P K G Y A A N Y C D G E C S F P L N A H M N A T N H A I V

A
   B
   C
   D                                                  x A T N H A I V
  hOD     P E G Y A A Y Y C E G E C A F P L N S Y M N A T
  hOE     P E G Y A A F Y C D G E C S F P L N A H M N A T

BMP-2A    Q T L V N S V N S K I P K A - C C V P T E L S A I S M L Y
BMP-2B    Q T L V N S V N S S I P K A - C C V P T E L S A I S M L Y
Vgr-1     Q T L V H L M N P E Y V P K P C C A P T K L N A I S V L Y

A                      N P E Y V P K
   B                                                            L Y
   C                                                            L Y
   D      Q T L V H F I N

BMP-2A    L D E N E K V V L K N Y Q D M V V E G C G C R
BMP-2B    L D E Y D K V V L K N Y Q E M V V E G C G C R
Vgr-1     F D D N S N V I L K K Y R N M V V R A C G C H

A
   B      L D E N E K V V L K N Y Q D M V V E G x G x R
   C      L x E Y D x V V L x N Y Q
   D
```

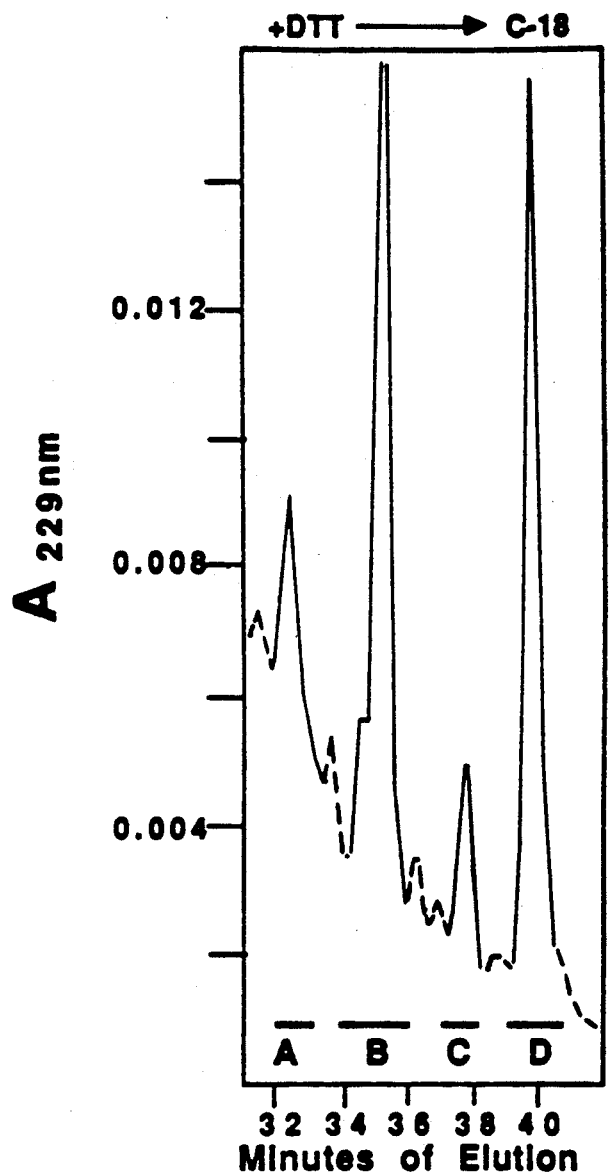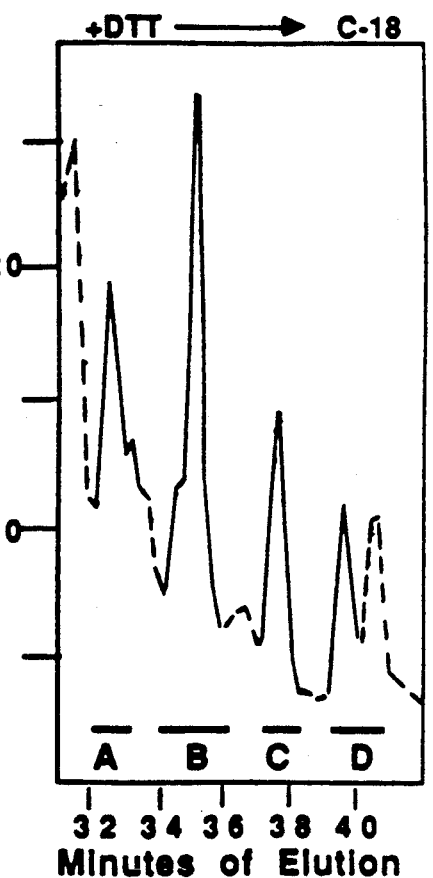

FIG.16A
FIG.16B
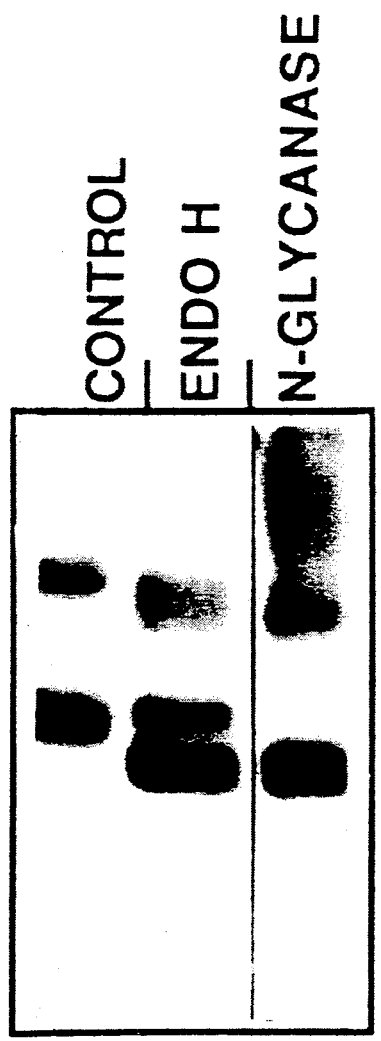
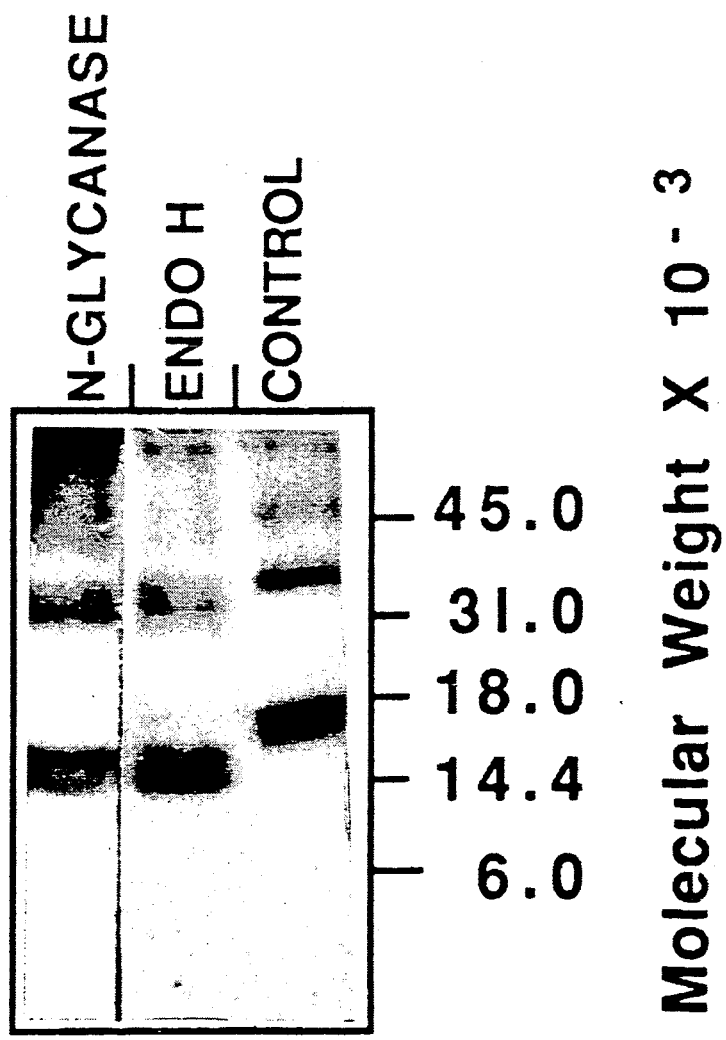

FIG. 17

| ODM-1 |
| :---: |
| S T G G K Q R S Q N R |

```
         10              20
A G G A A G C C T G C T C C A A G A C G C C A A G A A C
 Q   E   A   L   R   S   K   T   P   K   N 30              40
A G A A C A G C C T G C G G A T G C C A A C G T G C A G
 Q   N   S   L   R   M   P   N   V   Q 50              60              70              80
A G A A C A G C C A G C A G C G A C C A G G C A G G C A
 E   N   S   Q   S   D   Q   A   G   R

80
                   A G G C A G G C C G C C
                    R   Q   A   A 90             100             110
G T A A G A G C A G C G A G C T G T A T G T C A G C T T C C
 V   R   A   A   E   L   Y   V   S   F
</code>

210
  A C A T G A A C G C C A C C   ┌─────────────────┐
  Y   M   N   A   T            │ ODB-1           │
                                │ NHAIVQTLVHFIN   │
                                └─────────────────┘
```

FIG.18

ODM-1

```
        120                 130                 140
GGG ATC TGG ATG GCA GGA CTG GAT TAT AG
 R   D   L   W   M   A   G   D   W   I  I 150                 160                 170
CAC CAG AAG GAT ACG CTG CAT TTT ATT GTC
 A   P   E   G   Y   A   A   F   Y   C 180                 190                 200
ATG GAG GGA ATG TCT TTT TTC CAC TTA ACG CA
 A   D   E   W   C   S   F   F   P   L   N   A

210
ATA TGA ATG CC ACC C
 H   M   N   A   T
```

ODB-1

FIG.19A hOD  sKtpknQealRManVaenssSdQrQACKKHELYVSFRDLGWQDWIIAPEG
hOE  nKsssHQdssRMssVgdYnTSeQkQACKKHELYVSFRDLGWQDWIIAPEG hOD  YAAyYCeGECaFPLNsyMNAT
hOE  YAAfYCdGECsFPLNahMNAT

FIG.19B hOD  CtccAAgaCgccCAagaAcCAGGAagCCctgCGgATGGCCAacGTGGcAG
hOE  CaatAAatCcagCtctcAtCAGGAcTCCtccAgaATGtCCAgtGTtGGAG hOD  AgaAcAgCAgcAGcGAcCAgAggCAGGCCTGTAAGAAGCACGAgcTgTAT
hOE  AttAtAaCAcaAGtGAgCAaAaaCAaGCCTGTAAGAAGCACGAacTcTAT hOD  GTcAGCTTCCGaGAcCTGGGcTGGCAGGACTGGATcATcGCgCCTGAAGG
hOE  GTgAGCTTCCGgGAtCTGGGaTGGCAGGACTGGATtATaGCaCCAGAAGG hOD  cTACGCcGCcTacTAcTGTGAgGGgGAgTGTGCcTTcCCtCTgAACtCCt
hOE  aTACGCtGCaTttTAtTGTGAtGGaGAaTGTtCtTTtCCAcTtAACgCCc hOD  AcATGAACGCCACC
hOE  AtATGAATGCCACC

OSTEOGENIC FACTORS

This is a continuation-in-part of application Seri. No. 256,034 filed Oct. 11, 1988 now abandoned.

BACKGROUND OF THE INVENTION

The present invention relates to novel preparations of osteogenic factors, methods for their isolation and uses thereof (to repair bone defects). The preparations so isolated exhibit the ability to promote or stimulate the formation of bone at the site of their application. Bone is a highly specialized connective tissue with unique mechanical properties derived from its extensive matrix structure. A network of fibrous bundles composed of the protein, collagen, is presumed to provide the tension-resistant behavior of bone. In addition, other materials including proteoglycans, noncollagenous proteins, lipids and acidic proteins associated with a mineral phase consisting primarily of poorly crystallized hydroxyapatite are deposited in the extensive matrix architecture of bone. Bone tissue is continuously renewed, by a process referred to as remodeling, throughout the life of mammals. This physiologic process might serve to maintain the properties of a young tissue.

The processes of bone formation and renewal are carried out by specialized cells. Osteogenesis vis-a-vis morphogenesis and growth of bone is presumably carried out by the "osteoblasts" (bone forming cells). Remodeling oi one is apparently broug by an interplay between the activities of the bone-resorbing cells called "osteoclasts" and the bone-forming osteoblasts. The boney skeleton is thus not only an architectural structure with a mechanical function but also is a living tissue capable of growth, modeling, remodeling, and repair. Since these processes are carried out by specialized living cells, chemical (pharmaceutical/hormonal), physical and physiochemical alterations can affect the quality, quantity and shaping of bone tissue.

A variety of pathological disorders as well as physical stress (for example, fracture) necessitate active formation of bone tissue at rate that are significantly higher than that which can be supported by the normal milieu of the body. It is thus of value to identify physiologically acceptable substances (hormones/pharmaceuticals/growth factors) that can induce the formation of bone at a predetermined site where such substrances are applied, for example, by inplantation. Such agents could either provide a permissive matrix structure for the deposition of bone-forming cells, or stimulate bone-forming cells, or induce the differentiation of appropriate progenitors of bone-forming cells.

The presence of proteinaceous and prostaglandin-like growth stimulators for osteoblasts has been examined, see reviewsi Raisz, L. G . et al., The New England Journal of Medicine, Vol. 309, No. 1, pp. 29-35 (1983) and Raisz, L. G., et al., The New England Journal of Medicine, Vol. 309, No. 2, pp. 83-89 (1983).

The observation that a bone graft from the same individual or a compatible individual leads to the formation of new healthy bone at the site of the graft, led to the hypothesis that bone contains active proteins which promote local osteogensis. Urist, et al. disclosed evidence that bone matrix-associated noncollagenous proteins can be isolated by dissociative treatment of demineralized bone powder and that this mixture of noncollagenous proteins contain the local osteoinductive capability which was designated by Urist (e.g., Science, Vol. 150, p. 893 (1965)) as bone morphogenetic activity.

A variety of osteogenic, cartilage-inducing and bone-inducing protein preparations have been described in the art. Urist, et al. and others have described various partially fractionated protein preparations with osteoinductive properties. These preparations are fractionated from the noncollagenous protein mixture extracted using different dissociative treatment of demineralized bone powder and subjecting the extract to various protein fractionation steps. Several such preparations have been characterized by different assays to determine their biological activities and by protein components identified using different standard protein analytical methods.

Urist, et al., Proceedings of The Society for Experimental Biology And Medicine, 162, pp. 48-53 (1979), disclosed isolation of bone morphogenetic protein (BMP) from demineralized rabbit bone matrix. The reference discloses that BMP appears to contain a multitude of major protein components having molecular weights in the range of between 94,000 daltons (94K) to less than 14,000 daltons (14K) based on reducing SDS polyacrylamide gel electrophoretic (SDS-PAGE) analysis.

Urist, et al. in Proc. Nat'l. Acad. Sci. USA, Vol. 76, No. 4, pp. 1828-1832 (April, 1979), disclosed another preparation of BMP obtained from demineralized rabbit bone matrix. Five protein fractions each characterized by having a major component with an apparent molecular weight of 94K, 68K, 43K, 21K and 14.3K were identified by subjecting these preparations to SDS polyacrylamide gel electrophoresis. All five protein preparations were eluted from a gel column with o-methylmannoside. Four of the five preparations, namely those with major components of molecular weights ranging from 68K to 14.3K were eluted with ethyleneglycol and two preparations, namely those with major components of molecular weights from 21K and 14.3K were precipitated with calcium phosphate. All three groups of eluates were found to have comparable BMP activity. The reference suggests that the BMP activity in the third group (the preparations characterized by major components of 21K and 14.3K proteins) may result from dissociation of a low molecular weight hydrophobic molecule carried by a glycoprotein. The reference suggests the alternative possibilities that BMP could be a single glycoprotein molecule, that the biologic activity may be a function of a protein aggregate or that BMP activity may not be associated with bone glycoprotein at all (pg. 1831).

Urist, U.S. Pat. No. 4,294,753, disclosed that the molecular weight of BMP may range between about 20K and 63K (col. 4, lines 45-61). The reference disclosed that BMP preparation isolated from rabbit dentin matrix protein mixture appears to have a major component with a molecular weight of about 23K. Because a protein fraction obtained from osteosarcoma cells has a molecular weight of 63K, it was suggested that the matrix free 63K protein may be a BMP precursor.

Hanamura and Urist, et al., Clin. Ortho. and Rel. Res. No. 153 232-240 (November-December (1980), disclosed the purification of osteosarcoma produced material with bone morphogenetic activity into three main fractions characterized by having a major component of molecular weight of 16K, 12.5K and 7K, respectively. Fractions characterized by a major component with a higher molecular weight including a 22K protein were observed during initial purification steps; active fractions purified from such preparations did not contain the 22K protein. Based on these results, the 12.5K and 16K proteins were tentatively identified as BMP.

Conover and Urist, et al., The Chemistry and Biology of Mineralized Connective Tissues, Elsevier North Holland, Inc., Arthur Veis, editor, pp. 597–606 (1981), discloses the isolation of a BMP fraction from demineralized rabbit dentin. Preparations containing proteins having average molecular weights of 30K, 23K, 18K, 15K and 12K were identified. While it was suggested that a 23K protein might represent the active BMP fraction, it was acknowledged that the active fraction might be the 18K, 15K or 12K proteins which they were unable to separate from the 30K and 23K fractions.

Farley, et al., Biochemistry, Vol. 21, No. 14, pp. 3502–3507 (1982), discloses purification of a skeletal growth factor from demineralized human bone matrix with an apparent molecular weight of 83K. The disclosure makes reference to a 1981 reference (Trans. Annu. Meet.- Orthop. Res. Soc., 6, 136 (1981)) by Urist, Conover and others, describing bone morphogenetic protein as having a molecular weight of 23K.

Urist, et al., Clin. Ortho. and Rel. Res., No. 162, pp. 219–232, discloses a low molecular weight bone morphogenetic protein fraction extracted from bovine bone matrix and fractionated by ion exchange and gel chromatography. The reference discloses that bovine BMP may consist of components ranging in molecular weight from 12K to 30K with the main components corresponding to molecular weights of 23K, 18K and 12K. The reference suggests that the 18K component is the active protein of the group because of its invariable presence in active fractions.

Urist, et al., Proc. Soc. Exp. Biol. and Med., 173, pp. 194–199 (1983), identifies human bone morphogenetic protein (hBMP) extracted from demineralized human bone matrix as an 18K molecular weight protein. The 18K protein was identified as putative hBMP as a result of its invariable presence in chromatographic fractions having high hBMP activity and general absence in those fractions lacking such activity. 34K, 24K and 14K protein components isolated from the demineralized bone were found not to induce bone formation.

Seyedin, et al., U.S. Pat. Nos. 4,434,094, and 4,627,982 describe the work in Urist, U.S. Pat. No. 4,294,753 and state that in the Urist patent, BMP was not fully characterized. The Seyedin patents describe a process for partially purifying an osteogenic factor and describe the factors as having a molecular weight of less than or equal to 30K.

Urist, et al., Science, 220, pp. 680–686 (1983), again identifies BMP purified from demineralized bone matrix as an 18K molecular weight protein. Variable quantities of 14K, 24K and 34K proteins were isolated with the 18K protein but the reference discloses that each of the last three protein fractions can be removed without loss of BMP activity. The reference states that the 18K fraction is responsible for BMP activity and suggests that the 34K, 24K and 14K proteins are individually inactive but are subunits of a larger BMP complex with the 18K protein.

Urist, et al., Proc. Nat'l. Acad. Sci. USA, 81, pp. 371–375 (1984), confirms that bovine BMP has an apparent molecular weight of 18.5K daltons. The publication further discloses other bone derived proteins with apparent molecular weights of 17.5K and 17K, proteins with higher molecular weights of 34K, 24K and 22K and a protein with a lower molecular weight of 14K. The publication provided the N-terminal sequence for the 17.5K protein which had an unblocked amino terminus.

Urist, European Patent Application No. 212,474, discloses peptide fragments having molecular weights between about 4K and 7K comprising at least an active portion of the osteoinductive and immunoreactive domain of the 17.5K BMP molecule.

Wang, et al., Pat. Cooperation Treaty Application No. WO 88/00205, claiming priority based on applications including U.S. Ser. No. 880,776 filed Jul. 1, 1986, discloses a bovine bone inductive factor which is isolated from demineralized bone powder by a procedure comprising a number of chromatographic and dialysis steps. The bone inductive factor so isolated was found to contain, as judged by a non-reducing SDS-PAGE analysis, one or more proteins having a molecular weight of approximately 28,000 to 30,000 daltons. Reducing SDS-PAGE analysis of the active protein(s) yielded two major bands having the mobility of proteins having molecular weights of 18,000 daltons and 20,000 daltons respectively. Wang, et al. discloses three bovine proteins designated BMP-1, BMP-2 and BMP-3 where BMP is bone morphogenetic protein and provides peptide sequences for the proteins. Wang, et al. also discloses the nucleotide sequences and amino acid sequences predicted thereby of four human proteins designated BMP-1, BMP-2 Class I, BMP-2 Class II and BMP-3.

Wozney, et al., Science 242, pp. 1528–1533 (1988), describes the nucleotide sequences and amino acid sequences predicted thereby of three human complementary DNA clones (designated BMP-1, BMP-2A and BMP-3) corresponding to three polypeptides present in an extract of bovine bone which is capable of inducing de novo bone formation. Recombinant human BMP-1, BMP-2A and BMP-3 proteins were said to be independently capable of inducing the formation of cartilage in vivo. The nucleotide sequence and derived amino acid sequence of a fourth complementary DNA clone (designated BMP-2B) is also described. The BMP-1, BMP-2A, BMP-2B and BMP-3 proteins of this publication appear to correspond, respectively, to the BMP-1, BMP-2 Class I, BMP-2 Class II and BMP-3 proteins, respectively, of Wang, et al.

Sen, U.S. Pat. No. 4,804,744 issued Feb. 14, 1989, discloses a preparation of an osteogenic protein which is a member of the P3 family of proteins and which has an apaprent molecular weight of 22,000 to 24,000 daltons as revealed by coomassie blue staining of reducing SDS-PAGE analysis.

Lyons, et al., Proc. Nat'l. Acad. Sci. USA 86, pp. 4554–4558 (1989), describes the nucleotide sequence and derived amino acid sequence of a complementary DNa clone (designated Vgr-1) encoding a mouse protein which contains homologous regions for the deduced amino acid sequences of BMP-2A, BMP-2B and BMP-3.

Luyten, et al., J. Biol. Chem. 264, pp. 13377–13380 (1989), describes the purification and partial amino acid sequence analysis of a polypeptide present in an extract of bovine bone said to be capable of inducing de novo bone formation. This protein, designated osteogenin, has an apparent molecular mass of 22,000 daltons as judged by reducing SDS-PAGE analysis, and an apparent molecular mass of 30,000 to 40,000 daltons as judged by a non-reducing SDS-PAGE analysis. The amino acid sequences reported for osteogenin are said to show considerable homology to BMP-3 as described by Wozney, et al.

Bentz, et al., J. Bone and Mineral Res., 4 Supplement 1, p. S280 No. 650 (1989) and Bentz, et al., J. Cell Biol., 107, 162a No. 918 (1989) describe a protein material isolated from demineralized bone matrix said to promote osteoinduction in the rat. The osteoinductive factor (OIF) was identified as a glycoprotein and was said to exhibit osteoinductive activity only in the presence of TGF-$\beta$1 or TGF-$\beta$2. OIF had an apparent molecular mass of 22,000 to 28,000 daltons based on SDS gel electrophoresis and was identified as a monomeric molecule in light of the fact that reduction does not alter its mobility on SDS-PAGE.

SUMMARY OF THE INVENTION

The present invention is directed to mammalian bone matrix-derived proteins which exhibit the ability to promote or stimulate local osteogenesis (bone formation) at sites of implantation in mammals. Specifically, the invention provides preparations of osteogenic proteins and involves extraction and purification of such osteogenically active protein preparations including extraction of bone matrix proteins under dissociative (denaturing) conditions followed by further purification using one or more methods such as specific elution of these proteins from gel filtration chromatographic columns, ion-exchange chromatographic columns, metal chelate affinity columns, hydrophobic adsorption chromatographic columns and reverse phase HPLC (high performance liquid chromatography) columns using an acetonitrile gradient. These preparations obtained using such purification procedures are clearly characterized by their respective chromatographic behaviors using these gel filtration, ion-exchange, metal chelate, hydrophobic adsorption and reverse phase HPLC columns as well as by their ability to induce local bone formation in animals at a predetermined site where they are applied either alone or in admixture with a suitable pharmaceutically acceptable carrier. The invention further provides methods of inducing bone formation in a mammal comprising administering to the mammal effective amounts of the osteogenic preparation. Also provided are pharmaceutically acceptable compositions comprised of one or more of the proteins or active polypeptides in conjunction with a physiologically acceptable matrix material. The invention further provides polypeptide subunits of the osteogenically active 31,000 to 34,000 dalton protein molecules, designated P3 OF 31-34, which are found associated with the P3 proteins of bone nucleotide sequences encoding certain of the subunits of P3 OF 31-34 or portions thereof and novel osteogenically active heterodimer proteins comprising certain of these subunits.

BRIEF DESCRIPTION OF THE DRAWINGS

FIG. 6A represents the elution profile obtained by high performance liquid chromatography, on a reverse phase C18 column, of fragments of porcine P3 protein; the fragments were generated by the enzymatic digestion of reduced, carboxymethylated porcine P3 protein using Staphylococcus aureus V8 protease.

FIG. 10A shows the apparent molecular weight of the osteogenic factors as determined by non-reducing SDS polyacrylamide gel electrophoresis followed by silver staining.

FIG. 10B shows reducing SDS polyacrylamide gel electrophoresis of P3 OF 31-34 proteins followed by silver staining.

FIG. 11A shows the isolation of the subunits of the P3 OF 31-34 proteins (osteogenic factors) by reverse phase HPLC.

FIG. 11B shows the apparent molecular weights of the subunits as detected by silver staining of reducing SDS polyacrylamide gel electrophoretic analys.

FIG. 12 represents the alignment of the amino terminal and internal sequences of subunits A, B, C and D of the P3 OF 31-34 proteins with homologous regions from the deduced amino acid sequences of cDNA clones encoding hOD and hOE isolated according to the invention and the polypeptides designated in the literature as BMP-2A, BMP-2B and Vgr-1.

FIG. 14A shows the isolation and identification of subunits of the P3 OF 31-34 proteins eluting in fraction 26 from the reverse phase HPLC of the PS Pool.

FIG. 14B shows the isolation and identification of subunits of the P3 OF 31-34 proteins eluting in fraction 28 from the reverse phase HPLC of the PS Pool.

FIG. 16A shows reducing SDS polyacrylamide gel electrophoresis of reduced subunit A before and after treatment with either endo H or N-glycanase.

FIG. 16B shows reducing SDS polyacrylamide gel electrophoresis of reduced subunit D before and after treatment with either endo H or N-glycanase.

FIG. 17 shows the nucleotide and derived amino acid sequences of PCR-amplified DNA from U-2 OS mRNA, designated hOD.

FIG. 18 shows the nucleotide and derived amino acid sequences of PCR-amplified DNA from U-2OS mRNA, designated hOE.

FIG. 19A shows the homology between the derived amino acid sequences of the PCR-amplified sequences designated hOD and hOE.

FIG. 19B shows the homology between the nucleotide sequences of the PCR-amplified sequences designated hOD and hOE.

DETAILED DESCRIPTION OF THE INVENTION

Figure 1:
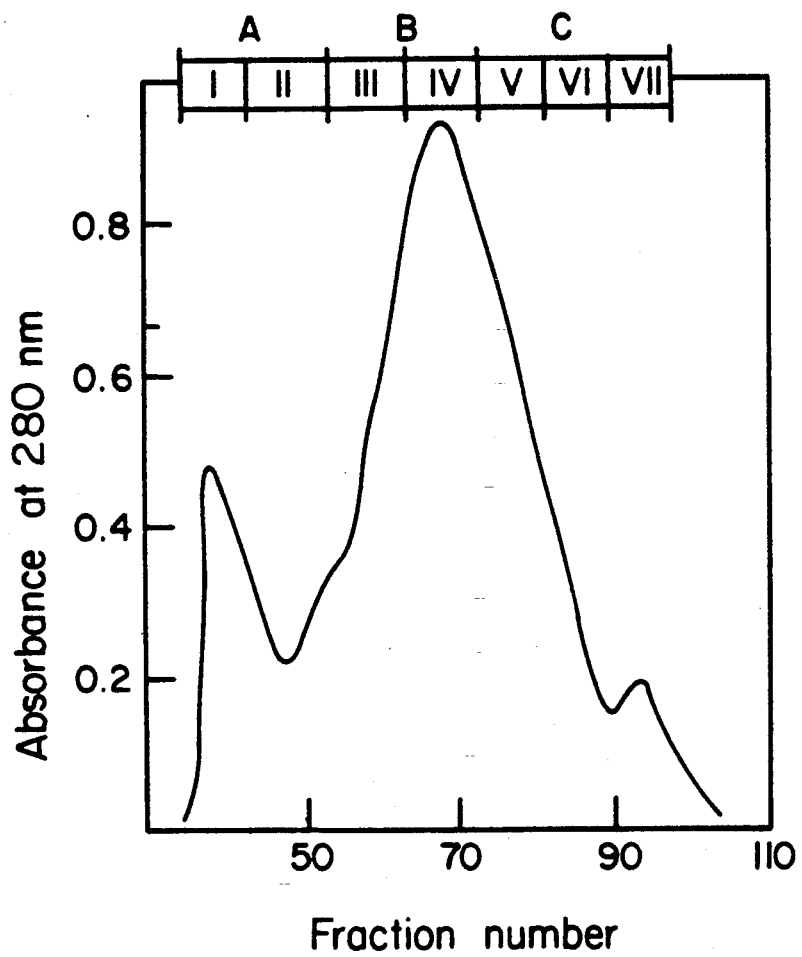
FIG. 1 represents the elution profile obtained by Sepharose CL-6B column chromatography of the proteins obtained in an eight hour extraction of demineralized calf bone powder with 4 M GuHCl-0.01 M Tris.HCl buffer (pH 7.0).

Using certain chromatographic procedures known in the art, each of several proteins have been purified starting from crude protein extracts of demineralized bone powder. As judged by the migration of these proteins in polyacrylamide gels under reducing conditions, using the procedure essentially as described in Laemmli, U.K., Nature, Vol. 227, pp. 680-685 (1970), different protein species have been assigned numbers such as P1, P2 and the like in the order of decreasing apparent molecular weight. Equivalent proteins have been obtained from bones of different mammals. The osteogenically active polypeptides of the invention have the characteristic that they copurify under certain purification procedures with a family of immunologically related P3 proteins, having an apparent molecular weight of 22,000 to 24,000 daltons. Similarly, a P3 protein isolated from human bone and purified according to the procedure essentially as described herein is immunologically related to the calf P3 protein and has an apparent molecular weight of 22,000 to 24,000 daltons revealed by coomassie blue staining of reducing SDS-PAGE analysis.

The osteogenically active preparation obtained using the method of this invention is sometimes referred to herein as the P3 protein. The invention further concerns the ability to obtain osteogenically active P3 proteins from bones of various mammals using the method of this invention. The osteogenically active protein preparations obtained from different mammalian bones using the method of this invention constitute member of a family of proteins, referred to herein as an immunologically related family of P3 proteins. The members of this family show substantial equivalence to each other with regard to characteristics such as (i) osteogenic activity, (ii) chromatographic characteristics in dissociative gel filtration columns, (iii) elution from hydrophobic reverse phase HPLC columns in acetonitrile, (iv) an essential homogeneity with regard to a molecular weight of between about 22,000 and 24,000 daltons revealed by coomassie blue staining of reducing SDS-PAGE analysis, (v) characteristics of certain major pept.d.ie fragments generated by proteolytic treatment and (vi) reactivity in an immunoassay directed toward certain immunogenic determinants characteristic in such preparations.

The invention further relates to the identification, in the P3 proteins, of proteins which, during gel filtration under non-reducing and dissociative conditions, elute as proteins having apparent molecular weights within the range of about 25,000 to 38,000 daltons, and more specifically, when analyzed by non-reducing SDS-PAGE followed by silver staining, migrate as proteins having apparent molecular weights within the range of about 31,000 to 34,000 daltons. These proteins are designated P3 OF 31-34, indicating osteogenically active 31,000 to b 34,000 dalton protein moleculares which are found associated with the P3 proteins of bone and are distinct from bone-derived protein molecules of similar molecular weight which lak osteogenic activity.

The invention further provides alternative protein fractionation methods of isolating these 31,000 to 34,000 dalton molecular weight protein constituents inherent in the P3 proteins which are characterized by the ability to promote osteogenesis. The P3 OF 31-34 osteogenic protein material yields four distinct peaks when analyzed by reverse phase HPLC after reduction. When analyzed by reduding SDS-PAGE and silver staining, three of the peaks are characterized as protein subunits migrating with apparent molecular weights within the range of 17,500 to 19,000 daltons, and the fourth peak is characterized as a protein subunit migrating with an apparent molecular weight within the ranté of 16,000 to 17,500 daltons.

Applicants have characterized the protein subunits of P3 OF 31-34 and designated them as subunits A, B, C and D. The subnits have been characterized by sequencing of various internal and presumptive amino-terminal polypeptide fragments. Applicants have utilized the polymerase chain reaction (PCR) technique to amplify sequences of human cDNA homologous to that encoding subunit D and have provided amino acid and nucleotide sequences for human subunit D (hOD). Applicants have also identified a sequence of human cDNA encoding what is characterized as polypeptide subunit E (hOE) which may be a new osteogenic polypeptide or may correspond to the bovine subunit A polypeptide. Applicants have also determined that the P3 OF 31-34 osteogenic protein material is comprised of polypeptide dimers including a heterodimer of subunit D with subunit B and a heterodimer of subunt A (and/or subunit E) with subunit B. The P3 OF 31-34 osteogenic material may further comprise heterodimers of subunit A (and/or subunit E) with subunit C and heterodimers of subunit D with subunit C given the high degree of homology (80%) between subunits B and C.

The invention provides polypeptide subunit D of P3 OF 31-34 such a isolated fro bovine bone and a purified and isolated nucleic acid from human DNA consisting of a nucleotide sequence encoding subunit D of P3 OF 31-34, a nucleotide sequence which encodes the same sequence of amino acids making up subunit D of P3 OF 31-34, a nucleotide sequence which is homologous with 80% of the nucleotides encoding subunit D of P3 OF 31-34 and a nucleotide sequence which would be homologous with 80% of the nucleotides encoding subunit D of P3 OF 31-34 but for the redundancy of the genetic code. The invention also provides recombinant expression systems for subunit D including vectors including nucleic acid sequences encoding subunit D of P3 OF 31-34, a cell transformed therewith and a polypeptide expression product of such a transformed cell.

The invention further provides polypeptide subunit E of P3 OF 31-34 and a purified isolated nucleic acid comprising a nucleotide sequence selected from the group consisting of a nucleotide sequence encoding subunit E of P3 OF 31-34, a nucleotide sequence which encodes the same sequence of amino acids making up subunit E of P3 OF 31-34, a nucleotide sequence which is homologous with 80% of the nucleotides encoding subunit E of P3 OF 31-34 and a nucleotide sequence which would be homologous with 80% of the nucleotides encoding subunit E of P3 OF 31-34 but for the redundancy of the genetic code. The invention also provides recombinant expression systems for subunit E including vectors including nucleic acid sequences encoding subunit E of P3 OF 31-34, a cell transformed therewith and a polypeptide expression product of such a transformed cell.

The invention also provides an osteogenic preparation comprising a dimer comprising subunit D of P3 OF 31-34 and, additionally, an osteogenic preparation comprising a heterodimer comprising subunits D and B of P3 OF 31-34 linked by at least one disulfide bond. The invention still further provides an osteogenic preparation comprising a dimer comprising subunit E of P3 OF 31-34 and, additionally, an osteogenic preparation compfising a heterodimer comprising su units E and B of P3 OF 31-34 linked by at least one disulfide bond. The invention further comprises an osteogenic preparation comprising a dimer comprising subunit A of P3 OF 31-34 and, additionally, an osteogenic preparation comprising a heterodimer comprising subunits A and B of P3 OF 31-34 linked by at least one disulfide bond.

The osteogenic protein preparations, namely the P3 protein, a preparation containing the P3 OF 31-34 protein or a preparation containig subunits A, B, C, D or E or homo- or heterodimers thereof as described herein, may be used to form a composition for implantation into a mammal by admixture with a physiologically acceptable matrix material. In addition, devices for implantation into mammals comprising a structural member encoated with the osteogenic factor/matrix composition are provided by the invention.

Ot may be possible, using procedures well known in the art, for example, chemical, enzymatic or rcombinant DNA techniques, to obtain polypeptides derived from the osteogenic proteins described herein which exhibit the ability to ptomote or stimulate osteogenesis. For exampoe, any of polypeptide subunits A, B, C, D and E or nucleic acid encoding such polypeptides or analogs not directly provided herein may be obtained according to procedures well inown to those skilled in the art. Such procedures include obtaining the complete amino acid sequence of any of the polypeptide subunits and screening DNA libraries from one or more mammalian species with polynucleotide probes based thereon, and including identifying cells expressing any of the polypeptide subunits prsent in P3 OF 31-34 by using a labelled antibody or oligonucleotide according to the present invention, isolating mRNA therefrom and preparign cDNA from the isolated mRNA. The invention further provides a process for the preparation of an osteogenic protein consisting of dimers of polypeptide monomers selected from the group consisting of P3 OF 31-34 subunit A, subunit B, subunit C, subunit D and subunit E. The process comprises the steps of culturing in suitable culture media one or more cell lines transformed with nucleic acid sequences encoding one or more polypeptides selected from the group consisting of P3 OF 31-34 subunit A, subunit B, subunit C, subunit D and subunit E. Dimers are then formed of the polypeptide monomers by linking them with at least one disulfide bond and the dimers so formed are then isolated.

Proteins or polypeptides that are or can be converted to osteogenically active species which are immunologically related to the P3 OF 31-34 proteins or subunits or fragments thereof are also considered to be within the scope of the present invention. Active entities, referred to herein as "active polypeptides", include any portion of the proteins or polypeptides which are the subject of the present invention and their functional derivatives which can be produced by conventional procedures such as chemical synthesis or recombinant DNA techniques. Active polypeptides further include deletions from, or insertions or substitutions of residues within the amino acid sequence of the osteogenic proteins and subunits. Combinations of deletion, insertion and substitution may also be made to arrive at the final construct, provided that the final construct possesses osteogenic activity. Derivatives of such active polypeptides can inclucde, for example, chemically or enzymatically modified polypeptides; fusion proteins; or polypeptides bound to a suitable carrier substance such as a polymer.

Natural sequence polypeptide subunits present in P3 OF 31-34 of one or more mammalian species or analogs and variants thereof may be praspred by direct chemical synthesis of polypeptide or by expression of DNA prepared by site-directed mutagenesis of subunit DNA or by chemical synthesis of oligonucleotide and assembly of the oligonucleotide by any of a number of techniques prior to expression in a host cell. [See, e.g., Caruthers, U.S. Pat. No. 4,500,707; Balland, et al., Biochimie, 67, 725-736 (1985); Edge, et al., Nature, 292, 756-762 (1981)]. Messenger RNA encoding P3OF 31-34 or analogs thereof may also be expressed in vitro. Changes in activity levels are measured by the appropriate assay. Modifications of such protein properties as redox or thermal stability, hydrophobicity, susceptiblity to proteolytic degradation, or the tendency to aggregate with carriers or into multimers are assayed by method well known to those of ordinary skill in the art.

Prokaryotic microorganisms (such as bacteria) and eukaryotic microorganisms (such as yeast) may be employed as host cells according to the present invention. *S. cerevisiae*, or common baker's yeast, is the most commonly used among eukaryotic microorganisms, although a number of other strains are commonly available. For expression in bacteria and yeast, cloning and expression vectors are well known to those skilled in the art, such aslambda phage and pBR322 in *E. coli* ad YRp7 in *S. cerevisiae*.

Cells derived from multicellular eukaryotes may also be used as hosts. Cells from vertebrate or invertebrate eukaryotes may be used, and those skilled in the art know of appropriate expression vectors for use therein, such as SV40 retroviral and papilloma viral vectors for mammalian host cells, NPV vectors for invertebrate host cells and Ti vectors for plant cells.

The present invention further discloses methods of using one or more of the proteins and/or active polypeptides and/or immunologically related entities as pharmaceutical agents for the stimulation of bone growth in mammals. Pharmaceutically acceptable compositions comprised of one or more of the proteins and/or active polypeptides and/or immunologially related entities in combination with a pharmaceutically acceptable carrier are also disclosed herein. Such compositions can optionally contain other bioactive materials or other ingredients which aid in the administration of the composition or add to the effectiveness of the composition.

As used herein, the term "immunologically related" is meant to include any polypeptide which shows binding and/or recognition to antigen-binding sites in antibodies raised or manufactured against the protein. The term "osteogenesis" means formation of new bone or induction of growth of pre-existing bones at specific sites in response to local administration (for example, implantation of an active preparation in a pharmaceutically acceptable manner). The term "osteogenic amount" refers to an amount of the osteogenic protein and/or active polypeptide and/or immunologically related entity sufficient to provide the desired effect. The term "osteogenically active" or "osteogenic" means that the preparation has the capability to promote or induce osteogenesis.

In addition, two unrelated protein preparations designated herein as P2 and P4 have also been isolated from bone of several different mammalian species. A family of P2 proteins, each member isolated from a particular mammalian bone source, has been characterized. A typical P2 protein isolated from calf bone has an apparent molecular weight of 30,000 to 33,000 daltons, but is incapable of inducing osteogenesis in the absence of the osteogenic protein associated with the P3 protein preparation. Immunologically related P2 protein has also been isolated according to the procedure essentially as described herein from human bone.

In a similar manner, a family of P4 proteins has been isolated according to the procedures described herein. In the stage of purification accomplished from calf bone, the P4 preparation consists of two major components which are incapable of inducing osteogenesis in the absence of the osteogenic protein associated with the P3 protein preparation, both having an apparent molecular weight of about 16,000 to 18,000 daltons and are characterized by amino terminus amino acid sequences as described later herein. Immunologically related members of this P4 protein family which are also incapable of inducing osteogenesis in the absence of the osteogenic protein have been isolated from human bone according to the procedures described herein.

The application of the osteogenic factors can be conveniently accomplished by administering, such as by implanting, a lyophilized preparation or suspension of one or more of the osteogenic proteins and/or one or more active polypeptide and/or one or more immunologically related entities in sufficient quantity to promote osteogenesis at the desired site. Alternatively, pharmaceutically acceptable compositions can be used which are comprised of one or more of the osteogenic proteins and/or one or more of the active polypeptides and/or one or more of the immunologically related entities described herein and a pharmaceutically acceptable matrix such as collagenous proteins or matrix material derived from powdered bone extracted with strong denaturing agents, or other pharmaceutically acceptable carriers.

The following examples are included to further illustrate the invention but are not to be construed as limitations thereon.

EXAMPLE 1

Isolation Of The Osteogenic Factors Bone Processing

In a typical preparation, long bones (ends of long bones) from a mammal (for example, ankles from calves, femur heads of verthebral column from human bones, the total tibia and fibula from rats) are processed and demineralized using well kinown conventional procedures such as those described in Urist, M. R., U.S. Pat. No. 4,294,753 (1981). These and all other references cited herein are incorporated herein by reference.

A convenient method of processing and demineralizing bone is as follows:

The periosteal layer surrounding the bone (preferably the bone is obtained from a young mammal and kept refrigerated until processing) is removed by mechanical means and then the marrow from the central cavity of the bone is removed by washing with cold water. The bone is pulverized into small particles [generally 1 to 2 millimeters (mm) in diameter] by conventional means, for example, using a Wiley mill. The particles are then washed extensively with a buffered saline solution such as a 0.15 M NaCl-0.1 M Tris.HCl buffer (pH 7.0) to remove most of the lipids and remaining blood. The particles are further reduced in size by shearing, for example, using a polytron homogenizer (Brinkman Instruments) so that particles of approximately 500 microns ($\mu$) in diameter or less are obtained. The homogenized particles are washed with buffered saline such as that noted above and water, then with ethanol and finally with ether. The washed homogenized particles are then vacuum or air dried; this "bone powder" can be stored at −80° C. for prolonged periods of time.

For efficient demineralization and protein extraction, the bone powder is sieved to obtain particles having a size range of about 75 to 500 $\mu$ in diameter. Demineralization (that is, the removal of calcium phosphate from the bone matrix) is achieved by repeated washes with a hydrochloric acid (HCl) solution, for example, by stirring bone powder for one hour with about 10 to 15 milliliters (ml) of 0.5 normal (N) HCl per gram (g) dry weight of bone powder, decanting the liquid and then repeated this process three or four times. The demineralized bone powder iis then washed extensively with deionized distilled water until the pH approaches neutrality. The water is removed from the demineralized bone powder by washing with ethanol, then ether, and then drying. The demineralized bone powder can be stored at ultralow temperatures (for example, −20° to −80° C.). Demineralization of the bone powder can also be accomplished using other well known procedures, for example, using a chelator such as ethylenediaminetetraacetic acid.

To determine if the treated bone powder is sufficiently demineralized after HCl treatment to be ready for the extraction of the bone-matrix proteins, the water-rinsed powder is tested for mineral content (that is, calcium content), for example, by the method of von Kossa, see J. von Kossa, Ziegler's Beitr. 29, 163 (1901)]. When the von Kossa stain is negative, the treated bone powder is sufficiently demineralized to be ready for the extraction of proteins.

Extraction and Separation of Proteins From Demineralized Bone Powder

Demineralized bone powder, prepared as described above, is extracted by constant stirring with an aqueous solution of about 2 to 8 molar (M) guanidium-hydrochlride (GuHCl) in a buffer such as Trizmahydrochloride (Tris-HCl) at or near pH 7.0 for a time sufficient to extract the desired proteins. Preferably, the extraction is performed by stirring tne demineralized boe powder with 4M GuHCl-0.01M Tris.HCl buffer (pH 7.0) in the presence of a proteolyti enzyme inhibitor suh as phenylmethylsulfonyl-fluoride for 8 to 12 hours (hrs) between about 4° to 20° C. The proteins from demineralized bone powder can be extracted by contacting the demineralized bone powder with an apppopriate GuHCl-Tris.HCl buffer for a time sufficient to obtain substantial quantities of the desired proteins. In a typical extraction of 100 grams of demineralized calf bone powder, approximately 1500 milligrams (mg) of total proteins are extracted in a three day extraction period with 4M GuHCl-0.01M Tris.HCl buffer (pH 7.0). In the process of the present invention, it has been found that more than 80 percent (%) of the total proteins obtained in a three day extraction can be extracted in the first 8 to 12 hrs with a 4 M GuHCl-0.01 M Tris.HCl buffer (pH 7.0). During the first 8 to 12 hrs of extraction, typically more than 95% of the total low molecular weight protein population that can be obtained in a three day extraction is recovered. Most osteogenic activity is associated with these low molecular weight proteins. About 15 ml of the 4M GuHCl-0.01M Tris.HCl buffer (pH 7.0) solution is used per gram dry weight of demineralized bone powder. After the extraction period is complete, the extract is filtered, for example, over Whatman paper, and the filtrate concentrated by conventional procedures; in typical experiments, an Amicon ultrafiltration apparatus (Amicon Corporation, Danvers, Mass.) with a membrane filter with molecular cut-off size of approximately 5,000 daltons is used for the concentration step (that is, the membrane retains molecules having a molecular weight greater than approximately 5,000 daltons, for example, an appropriate Diaflo ® ultrafiltration membrane such as YM-5).

The various buffers, for example, the 4M GuHCl-0.01M Tris.HCl buffer, the solutions, for example, the 0.5 N HCl solution, described herein are aqueous buffers or solutions in which the indicated materials are present in water at the indicated concenetration. The protein components of the concentrated proetin solution were fractionated using various conventional chromatographic techniques including high performance liquid chromatography (HPLC) as follows:

The initial protein fractionation was conveniently accomplished by chromatography on a Sepharose CL-6B (Pharmacia Chemicals, N.J.) column. In a typical experiment, the proteins extracted as described herein are concentrated by ultrafiltration to a concentration of about 25 to 40 mg/ml. The concentration of proteins in various extract preparations and column fractions were usually estimated by conventional means such as spectrophotometric measurement of the absorbence of the solutions at 280 nanometers (nm). An appropriate amount of protein concentrate (an amount providing approximately 500 mg of protein) was applied to a 5 centimeter (cm) × 90 cm Sepharose CL-6B column equilibrated with 4M GuHCl-0.01M Tris.HCl buffer (pH 7.0). The column is eluted with the 4M GuHCl-0.01M Tris.HCl buffer (pH 7.0) at a hydrostatic pressure head of between about 50 to 100 cm and individual fractions of 15 to 20 ml volume collected. A typical elution profile under the above conditions was obtained by measuring the absorbence of individual fractions at 280 nm and is shown in FIG. 1.

Figure 2:
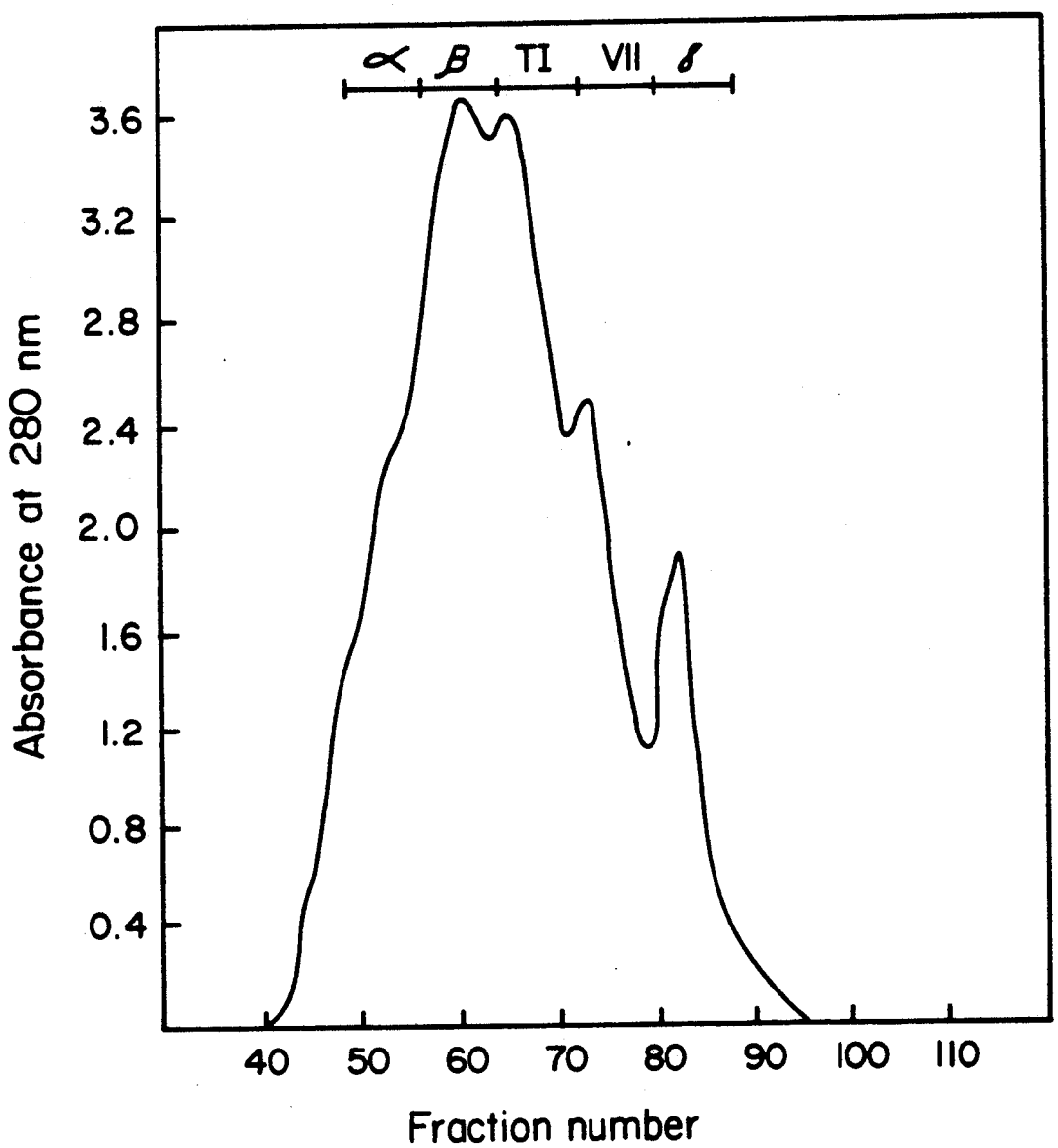
FIG. 2 represents the elution profile obtained by Sephacryl S-200 column chromatography, in 4 M GuHCl-0.01 M Tris.HCl buffer (pH 7.0), of the proteins contained in the active fraction obtained from Sepharose CL-6B column chromatography.

The bone inducing activity of various fractions eluted from the Sepharose CL-6B column was measured, using the bone induction assay system described herein, and indicated that the pool of fractions identified as "C" in FIG. 1 contained the factors responsible for the osteogenic activity. Pool C, which consisted of pooled fractions V, VI and VII, was concentrated using conventional procedures. In a standard extraction, pool C obtained from the elution of the total proteins on the Sepharose CL-6B column represents about 40% of the total proteins obtained in an 8 to 12 hr extraction of demineralized calf bones powder with 4M GuHCl-0.01M Tris.Cl buffer (pH 7.0). Further fractionation was then achieved by chromatography on a Sephacryl S-200 (Pharmacia Chemicals, New Jersey) column. In a typical experiment, 75 to 100 mg of proteins from pool C are applied at a concentration of approximately b 25 mg/ml to a 2.2 cm × 115 cm Sephacryl S-200 column and the column eluted with 4M GuHCl-0.01M Tris.HCl buffer (pH 7.0) under a hydrostatic pressure head of between about 50 to 75 cm ahd individiual fractions of approximately 4 ml in volume collected. A typical elution profile which was obtained under the above conditions is shown in FIG. 2.

Fractions from the Sephacryl S-200 column were pooled (see FIG. 2) and the resulting pooled materials arbitrarily identified as alpha (α), beta (β), gamma I (γI), gamma II (γII) and delta (δ).

Analysis of the proteins, using conventional discontinuous polyacrylamide gel electrophoresis in the presence of sodium dodecyl sulfate visualizing the protein bands by staining with coomassie blue [Laemmli, U.K., Nature, Vol. 227, pp. 680–685 (1970)], contained in the respective alpha through delta pools allowed identification of severla proteins. It was found that the alpha pool contained minor protein components of molecular ight highe than 50 000 daltons; the beta pool contained a major species at 38,000 to 40,000 daltons, some minor higher molecular weight contaminants, and small quantities of lower molecular weight protein species migrating between 14,000 and 30,000 daltson; the gamma I and gasmma II pools contained four major size class species migrating at 31,000 to 35,000 daltons, at 22,000 to 25,000 daltons, at 16,000 to 18,000 daltons, and at 12,000 to 14,000 daltons; the delta pool contained mostly proteins in the 12,000 to 14,000 dalton range.

Measurement of activity in the bone induction assay essentially as described herein indicated that the gamma I and gamma II pools contained factors inducing bone formation.

To simplify the discussions concerning the final purification of the osteogenic factors, a list of the protein species found in the beta, gamma and delta pools is presented in Table 1. As indicated previously, each of the respective major protein species was assigned an identifying code (P1, P2 and the like) as indicated in Table 1.

TABLE 1

| Major Species | | Minor Species | |
|---|---|---|---|
| Assigned Name | Estimated Molecular Weight × $10^{-3}$ | Assigned Name | Estimated Molecular Weight × $10^{-3}$ |
| P1 | 38–40 | | |
| P2 | 30–33 | | |
| | | PA | 28–30 |
| | | PB | 24 |
| P3 | 22–24 | | |
| | | PC | 19 |
| P4 | 16–18 | | |
| P5a | 13–14 | | |
| P5b | 14* | | |
| | | PD | 12 |

All primary molecular weight assignments of protein species are based on mobilities in discontinuous polyacrylamide gel electrophoresis with 13% acrylamide at pH 8.8 in the resolving gel in the presence of sodium dodecyl sulfate and a reducing presence of sodium dodecyl sulfate and a reducing agent. The minor protein species represented less than 10 to 15 percent of the total material in the respective samples analyzed on gels. *P5b migrates at about 10,000 daltons under non-reducing conditions which serves to distinguish P5a from P5b.

Reverse Phase HPLC Purification of the Osteogenic Preparation

A further purification step was carried out by reverse phase HPLC of the partially purified protein preparations, obtained from Sephacryl S-200 column chromatography, using a Beckman Altex HPLC controlled by a Model 421 microprocessor unit. Two approaches have been used.

A characteristic feature of some of the isolated proteins, especially the P3 protein family described herein and the osteogenically active protein preparation copurifying therewith is the lack of solubility in the absence of a strong dissociating agent such as GuHCl. In addition, when multiple protein species were simultaneously present in a pool, the removal of GuHCl resulted in a coprecipitation of other proteins along with the P3 proteins including the P3 0F 31-34. A method was, therefore, developed where narrow pools consisting of only one or two major proteins were obtained from the Sephacryl S-200 column and used as the starting material for further purification by HPLC. In addition, in order to maximize the retention of proteins in solution, pools such as the ones described above were dialyzed directly against an aqueous solvent containing 0.1% trifluoroacetic acid (TFA) supplemented with acetonitrile (ACN) at concentrations of between 10% to 15% by volume. A conventional dialysis membrane tubing with molecular weight cut-off size of 3,500 daltons or lower is conveniently used in this procedure.

Figure 3A:
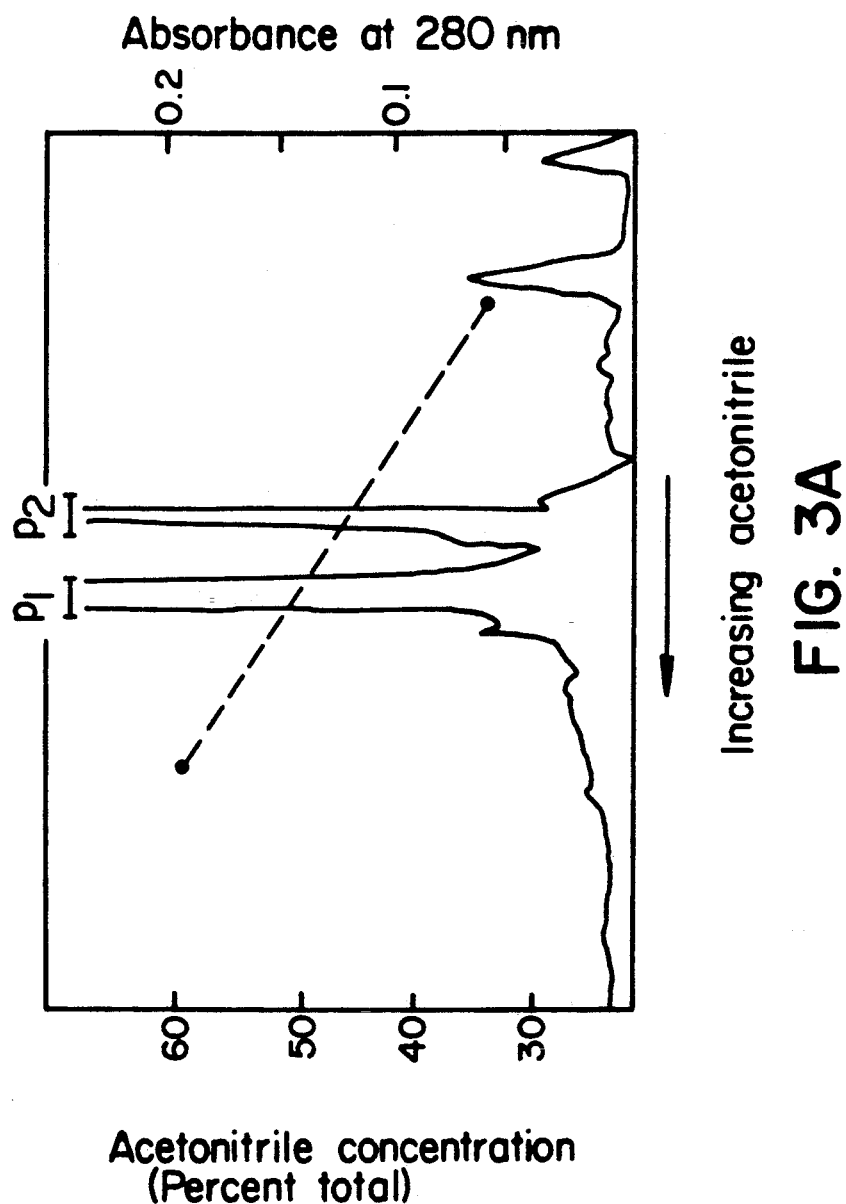
FIG. 3A reprsents the elution profile of proteins present in the active pool from Sephacryl S-200 column chromatography on a reverse phase Protesil 300 octyl column using an acetonitrile gradient for the elution of proteins.

Proteins soluble in the TFAiACN solvent could then be conveniently obtained by removal of the insoluble material from each dialyzed pool by centrifugation. The soluble proteins at this point could be chromatographed on a reverse phase HPLC column such as the Protesil 300 octyl column described herein. In a typical experiment, the TFAiACN soluble proteins obtained from the peak fractions in this manner were applied to a 0.46 cm × 25.0 cm Protesil 300 octyl column (Whatman) of 10 micron particle size equilibrated with 0.1% TFA:10% ACN. Proteins bound to the column under these conditions were eluted at a flow rate of 60 ml/hr using a linear 10% to 80% ACN gradient developed over 45 minutes. In a typical experiment, as indicated in FIG. 3A, P2 and P1 proteins were sequentially recovered with increasing ACN concentrations (depicted by the dashed line) from the gamma I peak. Similarly, P1 protein can be obtained from the beta peak while P5a and P5b are obtained from the delta peak. The P3 protein and the osteogenically active protein associated therewith elute between the gamma I and gamma II regions of the Sephacryl S-200 column. The P3 and P3 OF 31-34 protein preparation is found in both the soluble and the insoluble materials obtained by dialysis of appropriate functions against TFAiACN. The lack of solubility of the P3 and P3 OF 31-34 proteins thus yields osteogenically active protein in the presence of substantially purified P3 protein in the insoluble material. The P3 and P3 OF 31-34 proteins retained in solution in the TFAiACN solvent can be further purified by reverse phase HPLC essentially as described above.

Figure 3B:
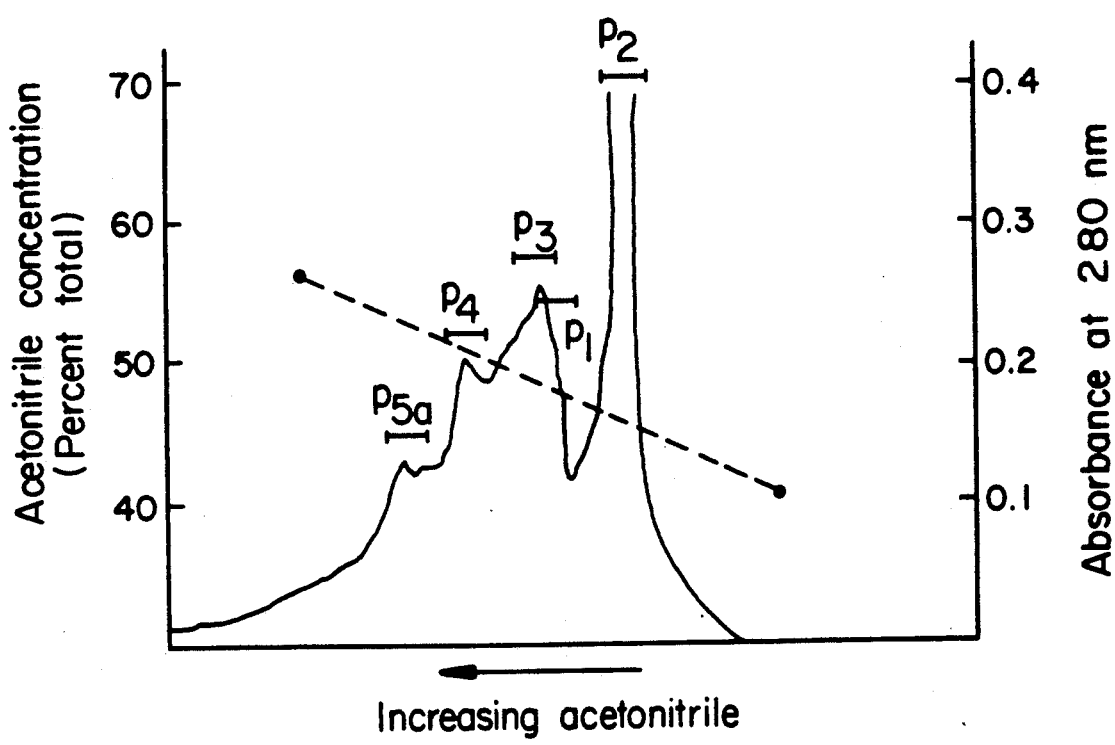
FIG. 3B rpresents the elution profile of proteins present in the active pool from sephacryl S-200 column chromatography on a reverse phase Protesil 300 octyl column using an acetonitrile gradient for the elution of proteins.

The second procedure to purify proteins to an essentially homogeneous state was designed to take advantage of the high degree of insolubility of certain proteins in the 35,000 to 14,000 dalton range, especially when they are present together at high concentrations (for example, approximately 10 mg/ml). In this procedure, proteins eluting in the gamma I and gamma II pools from the Sephacryl S-200 column chromatography (that is, the pools where the bone inducing activity is found) were concentrated to approximately 10 mg/ml. The material was rapidly dialyzed [for example, six changes each of 4 liters every 2 to 3 hrs, (using dialysis tubing with a molecular cut-off size of 2,000 daltons)-]against deionized distilled water at 15° to 23° C. Precipitated proteins were collected by centrifugation and washed several times with deionized distilled water keeping the concentration of protein at higher than 10 mg/ml of washing water. The principal constituents of this precipitated material were found to be P2, P3, P4 and P5a; small amounts of P1 protein was found in variable quantities in some cases. The final pellet was dissolved in 0.1% TFA with 15% ACN and the solubilized material was applied to a Protesil 300 octyl column. Increasing ACN concentration eluted the P2, P4, P5a and P3 proteins as shown in FIG. 3B, a typical elution profile.

Each of the major protein species described in Table 1 was further purified by rechromatographing on the Protesil 300 octyl column. Pools of fractions obtained as indicated in FIG. 3 were concentrated by lyophilization and redissolved in 0.1% TFA and about 10 to 20% ACN depending upon the particular lyophilized material and reapplied to the Protesil 300 octyl column. The proteins were eluted from the column using a linear 10% to 80% ACN gradient at a flow rate of 60 ml/hr under conditions as previously described herein except that the proteins were eluted over a longer period, thus resulting in numerous individual fractions. The purity of each of the protein fractions was determined using conventional discontinuous PAGE. Those fractions which showed only one major species were used for further chemical and biological characterizations. Typically, these fractions were lyophilized and stored as lyophilized powders.

Figure 4:
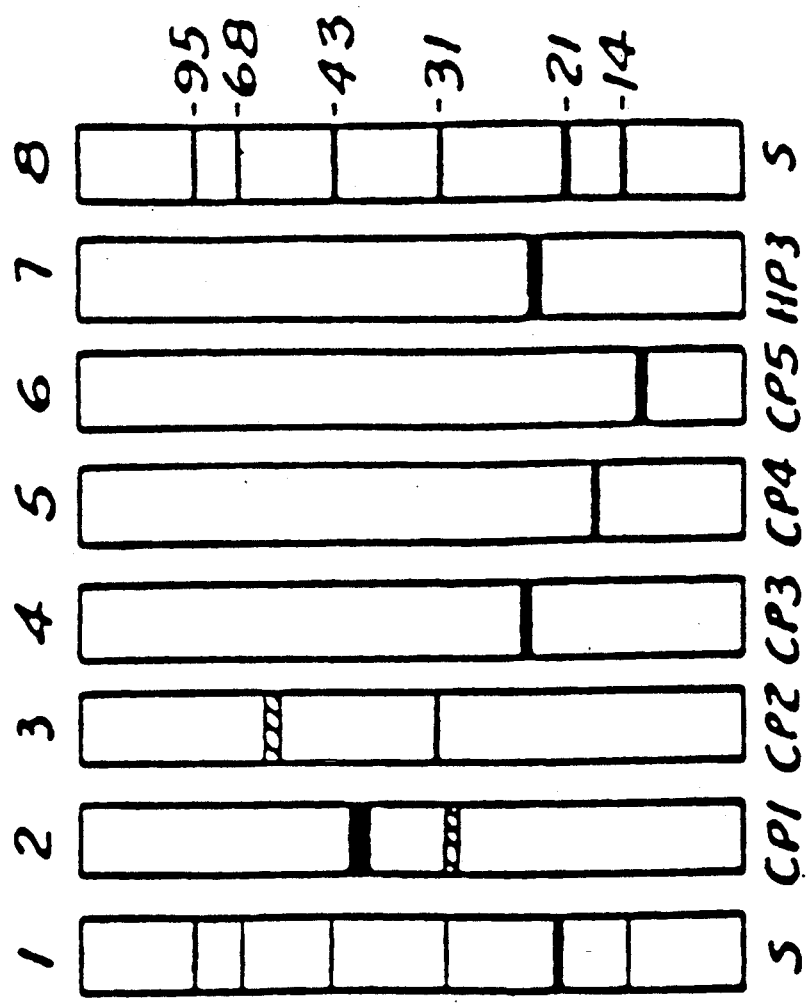
FIG. 4 represents the results of electrophoretic analysis of purified bone matrix proteins on discontinuous sodium dodecyl sulfate-polyacrylamide gels in the presence of a reducing agent followed by coomassie blue staining to detect the protein material.
Figure 5A:
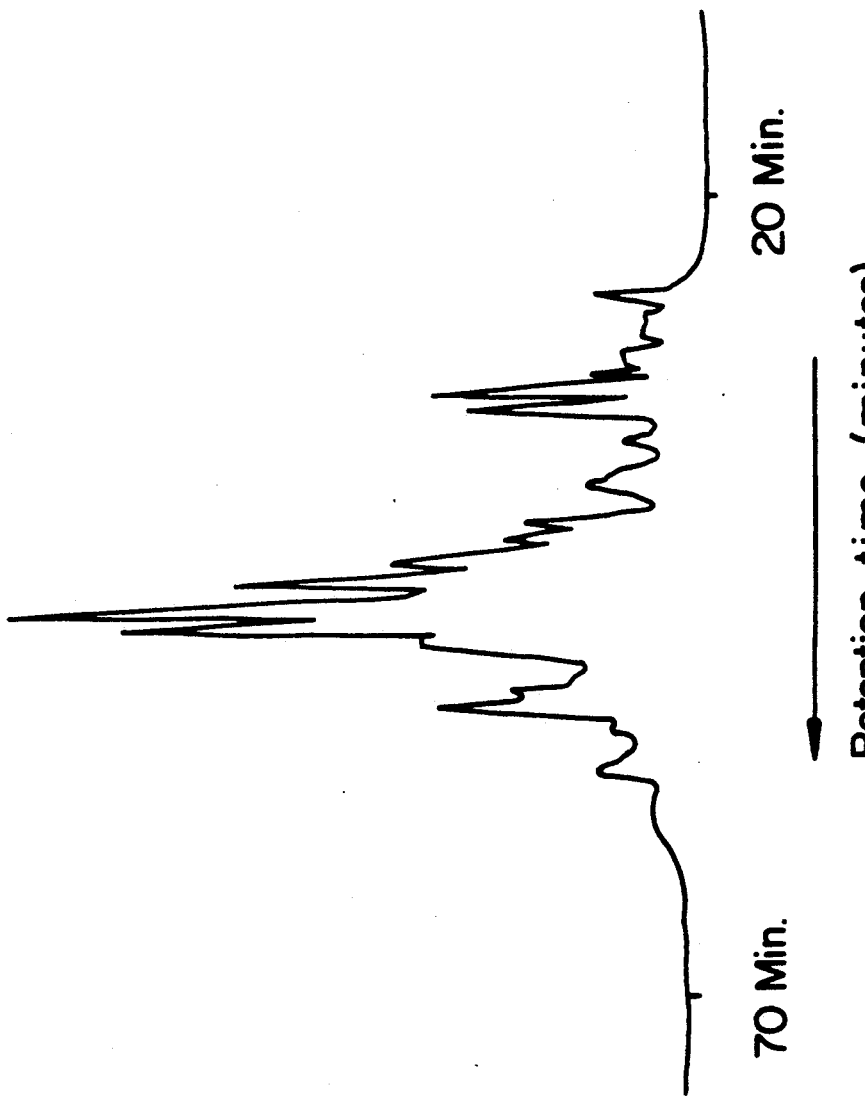
FIG. 5A represents the elution profile obtained by high performance liquid chromatography, on a reverse phase C8 column, of fragments of porcine P3 protein; the fragments were generated by the enzymatic digestion of porcine P3 protein using Staphylococcus aureus V8 protease.
Figure 5B:
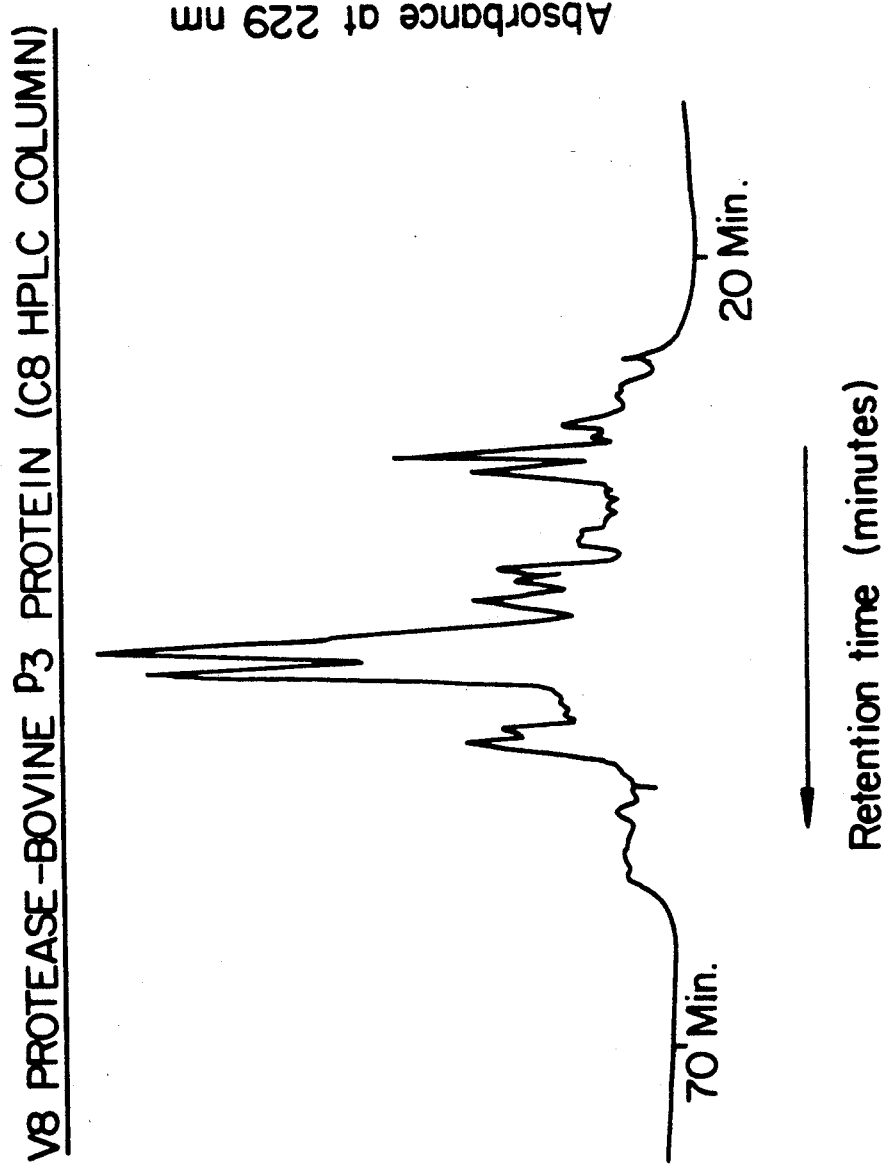
FIG. 5B represents the elution profile obtained by high performance liquid chromatography, on a reverse phase C8 column, of fragments of bovine P3 protein; the fragments were generated by the enzymatic digestion of bovine P3 protein using Staphylococcus aureus V8 protease.
Figure 6B:
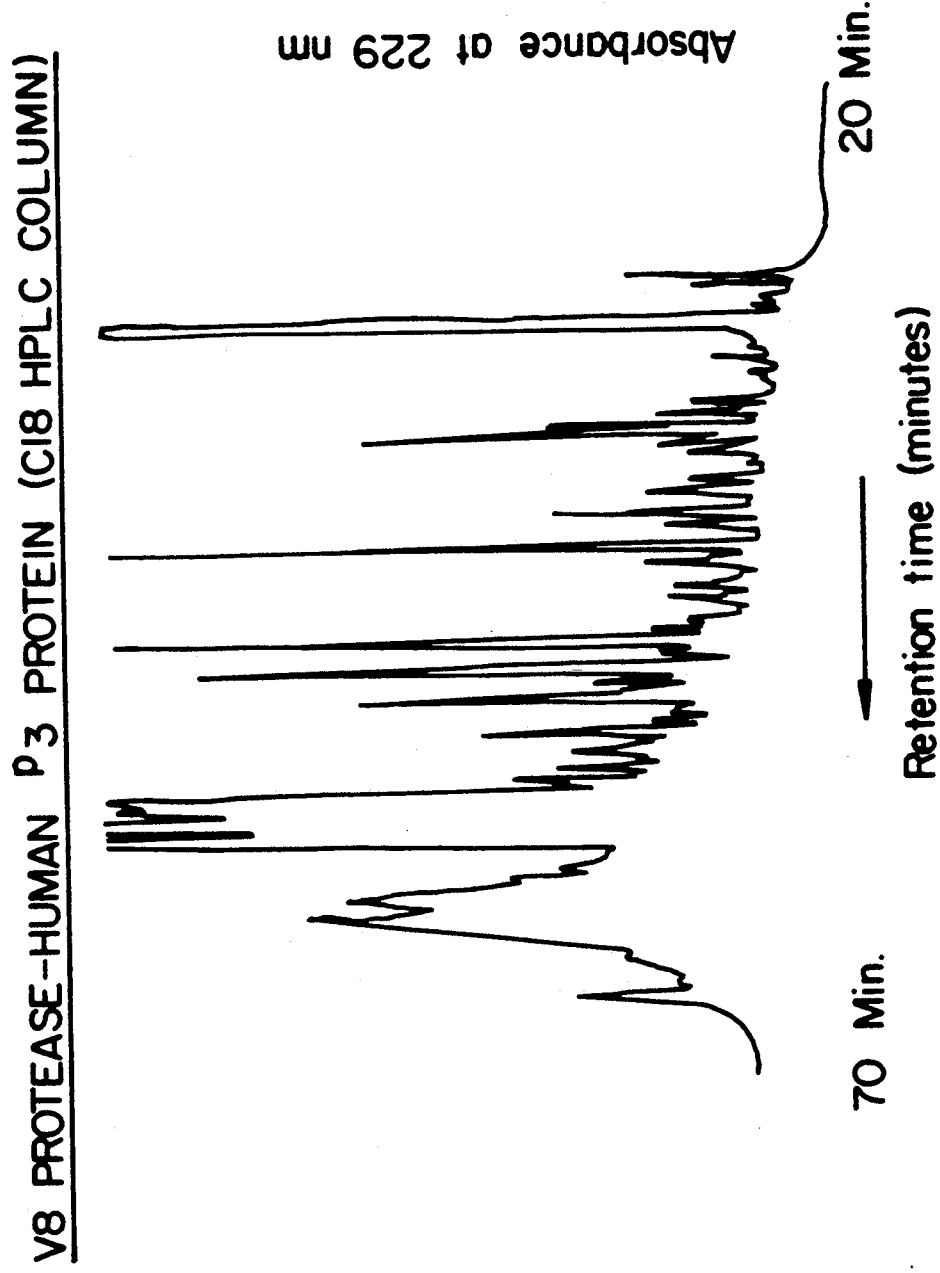
FIG. 6B represents the elution profile obtained by high performance liquid chromatography, on a reverse phase C18 column, of fragments of human P3 protein; the fragments were generated by the enzymatic digestion of reduced, carboxymethylated human P3 protein using Staphylococcus aureus V8 protease.
Figure 7A:
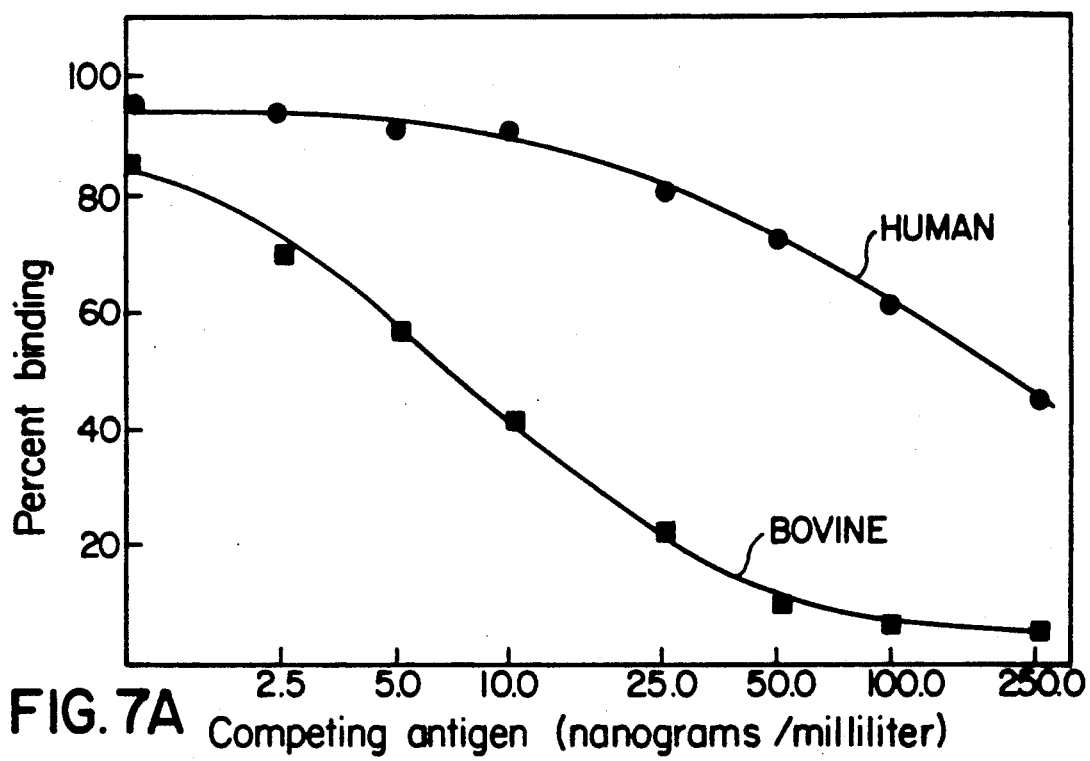
FIG. 7A represents the results of competitive radioimmunoassays measuring the ability of radiolabelled test antigen to bind to specific antibody molecules in the presence of competing unlabelled antigen preparations.
Figure 7B:
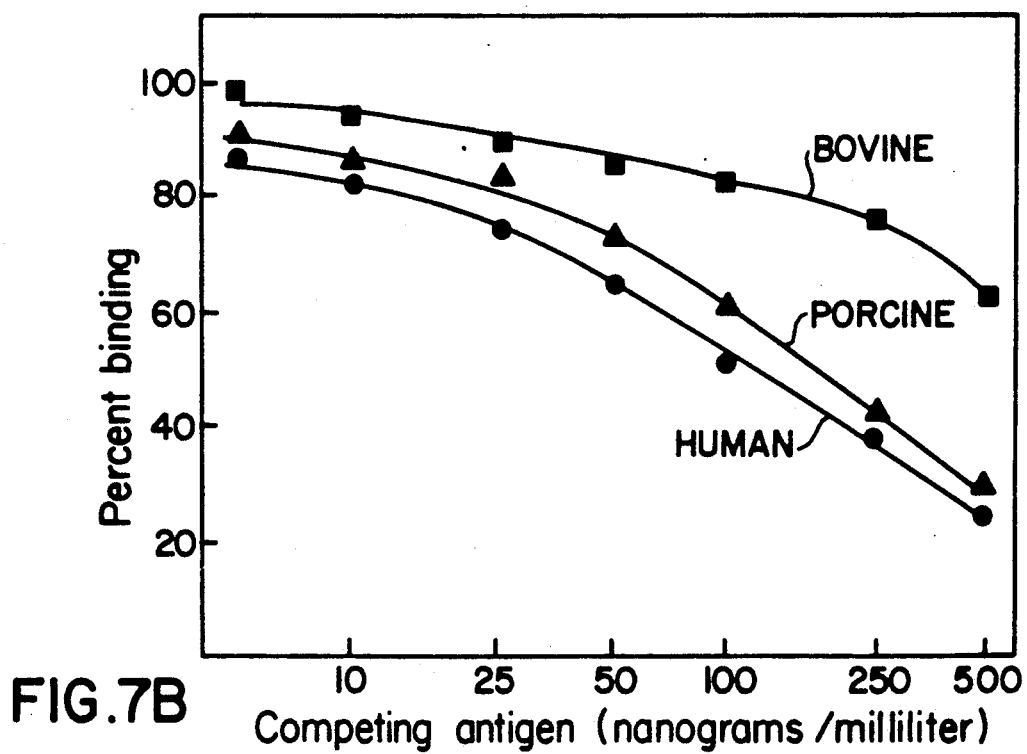
FIG. 7B represents the results of competitive radioimmunassays measuring the ability of radiolabelled test antigen to bind to specific antibody molecules in the presence of competing unlabelled antigen preparations.
Figure 7C:
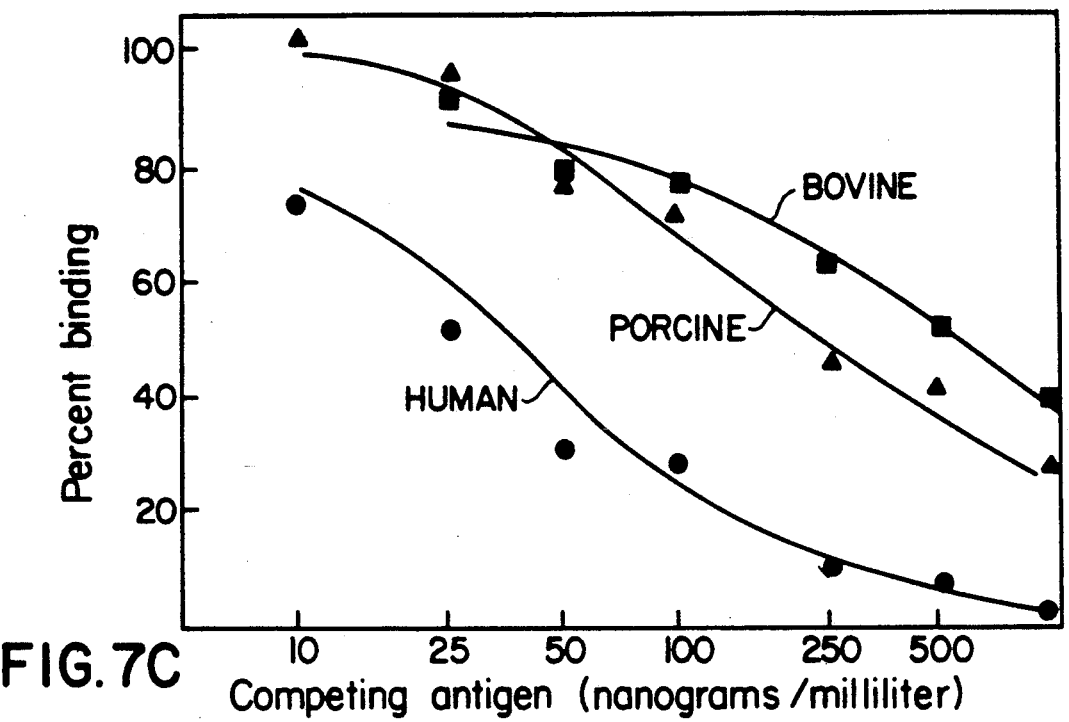
FIG. 7C represents the results of competitive radioimmunoassays measuring the abiliyt of radiolabelled test antigen to bind to specific antibody molecules in the presence of competing unlabelled antigen preparations.
Figure 7D:
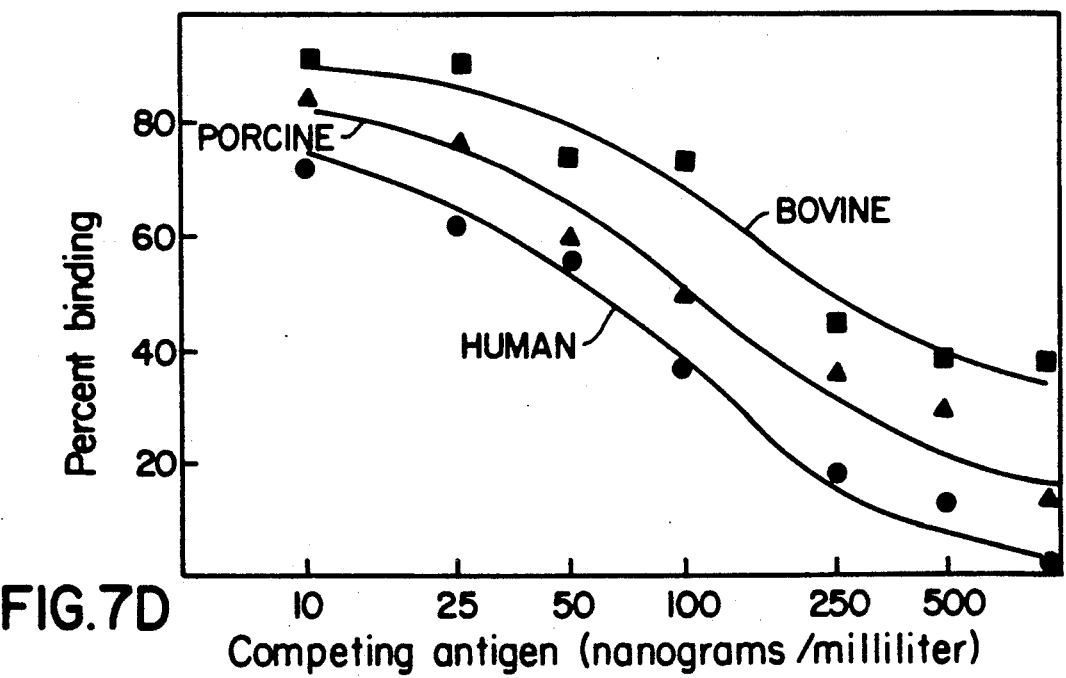
FIG. 7D represents the results of competitive radioimmunoassays measuring the ability of radiolabelled test antigen to bind to specific antibody molecules in the presence of competing unlabelled antigen preparations.
Figure 8:
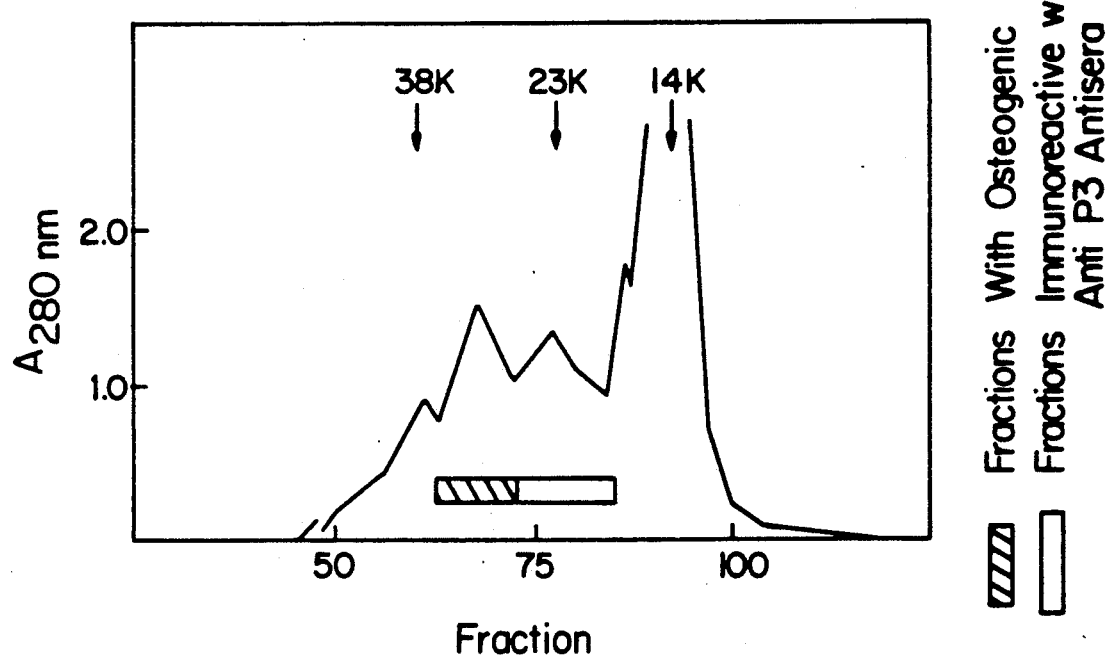
FIG. 8 represents the elution profile obtained by Sephacryl S-200 column chromatography, in 4 M GuHCl-0.01 M Tris.HCl buffer (pH 7.0), of the proteins contained in the active 5K-100K fraction.

FIG. 4 depicts the results of a typical discontinuous gel electrophoretic analysis on sodium dodecyl sulfate-polyacrylamide gels. The analysis was performed on a discontinuous polyacrylamide gel system in the presence of sodium dodecyl sulfate and a reducing agent where the resolving gel was 13% in acrylamide and 0.35% in bis-acrylamide crosslinker at a pH of 8.8. The gel was run at 50 volts for 30 minutes followed by 7 hrs at 100 volts. Protein bands were visualized by staining with coomassie brilliant blue R. Columns 1 and 8 depict gels with the following standard molecular weight markersi 95,000 (phosphorylase A), 68,000 (bovine serum albumin), 43,000 (ovalbumin), 31,000 (carbonic anhydrase), 21,000 (soybean trypsin inhibitor), and 14,000 (ribonuclease); columns 2, 3, 4, 5 and 6 show, respectively, the P1, P2, P3 (including the P3 OF 31-34 protein), P4 and P5 protein (CP1 through CP5) from demineralized calf bone powder; and column 7 the P3/osteogenic protein (HP3) from demineralized human bone powder. Portions shaded with oblique lines are bands of low concentration.

The calf and the human protein preparations comprising the P3/osteogenic proteins each, when implanted in rats following the bioassay system described herein, induces the formation of bone at the implant site in approximately 3 weeks. It appears that the osteogenic proteins which copurify with the members of the P3 protein family isolated from different mammals will show osteogenic activity in mammals in general. Thus, the P3 proteins represent a family of immunologically related proteins which copurify with the primary osteogenic factors according to the above methods.

Bone Induction Assay System

To determine the osteogenic activity of test protein fractions or proteins a procedure such as the following can be used. Bone matrix powder (75 to 500 μm size) is demineralized as described herein and then extracted sequentially three times, each with 15 to 20 ml of 4M GuHCl per gram of demineralized bone powder. The extracted matrix is extensively washed with water, followed by ethanol and ether and then the powder is dried. This powder, when implanted in a test animal, such as a rat, does not induce osteogenesis and is called inactive bone matrix (IBM). In order to measure the activity of a protein preparation, the IBM power is mixed with an aqueous solution or suspension of the protein and the water removed by lyophilization. The reconstituted matrix is then packed in gelatin capsules and implanted subcutaneously near the thigh muscles of young (one to two months old) rats. Varying amounts of protein preparations are used together with a constant amount of IBM in each capsule to determine the efficacy of the different protein preparations. Osteogenic activity in each implant is estimated by two approaches, (a) measuring the level of the enzyme alkaline phosphatase in the implant tissues at 17 to 20 days following implantation and (b) performing a histologic examination of a 5 to 7 micron thick section of the tissue developed at the implant site following staining of paraffin-fixed sections of this tissue with toluidine blue (stains cartilage matrix and bone matrix), hematoxylin-eosin (resolves fibrous, cartilaginous and bone tissues) and von Kossa silver stain (for calcified matrix of bone tissue).

The level of alkaline phosphatase i measured since active bone formation is characteristically preceded by a significant surge of this enzyme and continued formation of bone is accompanied by a stable elevated level of alkaline phosphatase activity compared to that found in non-bone fibrous tissue surrounding the implants. An approximate quantitation of the levels of bone inducing activity in a protein preparation has been obtained by quantitating the level of alkaline phosphatase per unit weight of implant tissue. In practice, the implant tissue is homogenized in an appropriate buffer such as Tris-saline, dissociated with a nonionic detergent and the solubilized enzymes that are released from the tissue are obtained by removing the debris using centrifugation. The levels of alkaline phosphatase are quantitated by measuring the conversion of paranitrophenylphosphate to paranitrophenol catalyzed by dilutions of the test extract and calculating from a standard curve of known enzyme activity.

In bioassay studies, protein pools from the Sephacryl S-200 column were reconstituted with IBM and implanted subcutaneously in rat thighs. Measurement of alkaline phosphatase activity and histological evaluation of sections of explants removed 17 to 20 days after implantation, showed that the P1 and the P5a-P5b proteins do not have bone inducing activity. The bioassay studies indicated the presence of maximum osteogenic activity in proteins in pools gamma I and gamma II. The three major components of the gamma fractions, that is, the P2 protein, the P3 and P3 OF 31-34 protein and the P4 proteins were purified using reverse phase HPLC as described above. The purified proteins, either singly or in a complete mixture, were reconstituted with inactive bone matrix and a bone induction assay performed. The results are shown in Table 2.

TABLE 2

| | Alkaline Phosphatase (units/g) | Histology |
| --- | --- | --- |
| IBM* Alone | <5 | Fibrous Tissue |
| IBM + 750 μg P2 protein | <5 | Fibrous Tissue |
| IBM + 750 μg P3 protein (including the P3 OF 31-34 protein) | 78 | New Bone |
| IBM + 1000 μg P4 protein | <5 | Fibrous Tissue (a small trace of cartilage) |
| IBM + 250 μg each of P2, P3 (including the P3 OF 31-34 protein) and P4 proteins | 63 | New Bone |

*"IBM" means Inactive Bone Matrix.
"<" means less than.

The data in Table 2 indicate that the P3 protein (including the P3 OF 31-34 protein) alone induced the formation of bone. Implants containing the P3 and P3 OF 31-34 preparation developed into tissues that contained high levels of alkaline phosphatase enzyme activity. In contrast, implants prepared by reconstituting with either the P2 or the P4 preparation failed to produce detectable bone. When all three preparations were used in combination, significant bone formation was observed and high levels of alkaline phosphatase enzyme were obtained with one-third the amount of P3 protein preparation (as compared to the P3 protein implant alone). It thus appears that at low concentrations of P3 protein preparation including P3 OF 31-34, the presence of the P2 and/or the P4 protein provides enhancement of osteogenesis induced by the P3 protein preparation.

In using the active preparations described herein, an osteogenic amount of the protein and/or active polypeptide and/or immunologically related entity, with or without a pharmaceutically acceptable carrier, is administered at or in the proximity of the site in the mammal at which bone induction is desired. Administration will depend on the age, condition, sex and other characteristics of the subject to be treated. Preferred administration is by implantation, local injection or time controlled delivery using the site and configuration of the area to be healed, such as, for example, a fracture zone. For example, a 5 cubic millimeter bone chip can be obtained with about 100 to 200 micrograms ($\mu$g) of P3 protein administered or implanted locally in the form of an implant in about 100 mg of IBM.

Active preparations can include other suitable bioactive materials such as growth factors, chemotactic agents, steroids, antibiotics, anti-inflammatory agents and the like.

Also provided by the present invention are alternative methods whereby the osteogenic protein present in the preparation purified according to Example 1 may be treated so as to isolate the P3 OF 31-34 protein which is of extremely high purity and osteogenic potency.

The process of Example 1 for obtaining the P3 family of immunologically related protein included a demineralization step, a guanidine extraction step, a size fractionation step in non-reducing denaturing solvents, a dialysis step and a reverse phase HPLC step. An improvement of the size fractionation step involved the use of molecular sizing filters which could fractionate very large volumes of material and yield a molecular weight cut between 5,000 or 10,000 daltons and 100,000 daltons (5K-100K or 10K-100K). A second improvement of the size fraction step relied on the pooling of protein fractions eluting within narrower molecular weight ranges from a gel filtration chromatography column (Sephacryl S-200) run in a non-reducing denaturing solvent. Using the S-200 column, the osteogenic activity was eluted within the region corresponding to a molecular weight range of 25,000-38,000 daltons, whereas the $\gamma$I and $\gamma$II pools used to purify the P3 protein had a molecular weight range of 14,000-40,000 daltons wherein the material immunoreactive with the antibodies directed against the major immunogenic determinants in the P3 protein migrated between the molecular weight range of With use of these improvements to the process, the osteogenic activity eluted from reverse phase HPLC columns within the same concentrations of acetonitrile as those concentrations of acetonitrile required to elute the P3 family of related proteins. Reverse phase HPLC of the S-200 active pool (eluting within the molecular weight range of 25,000-38,000 daltons) allow further resolution of these components of P3 protein which could be subfractionated using additional or different fractionation steps.

Fractionation of the osteogenically active pool of 25,000-38,000 dalton proteins using DEAE ion-exchange chromatography columns (Pharmacia Chemicals, N.J.) showed that the osteogenic activity does not bind to the DEAE column at pH 6.5 and thus could be separated from material which bind to DEAE-column. protein preparation has been achieved using chromatofocusing columns (Pharmacia Chemicals, N.J.) whereby the activity is recovered at an apparent pH of 7.5 or greater. This extended purification work of osteogenically active molecules in P3 proteins has also indicated that the osteogenic activity was distinct from the TGF-beta and TGF-beta immunoreactive material. The osteogenic activity bound binds to a Mono-S FPLC (Fast Protein Liquid Chromatography) column (Pharmacia Chemicals, New Jersey) equilibrated at pH 6.5 and can be eluted at a NaCl concentration greater than that required to elute the TGF-beta or TGF-beta immunoreactive material. It was also found that the osteogenic activity in the S active pool eluted from Mono-S column again could be characterized by its elution from a reverse phase HPLC column within the same concentrations of acetonitrile required to elute the P3 proteins.

EXAMPLE 2

Purification of Bovine Osteogenic Factors

Figure 9:
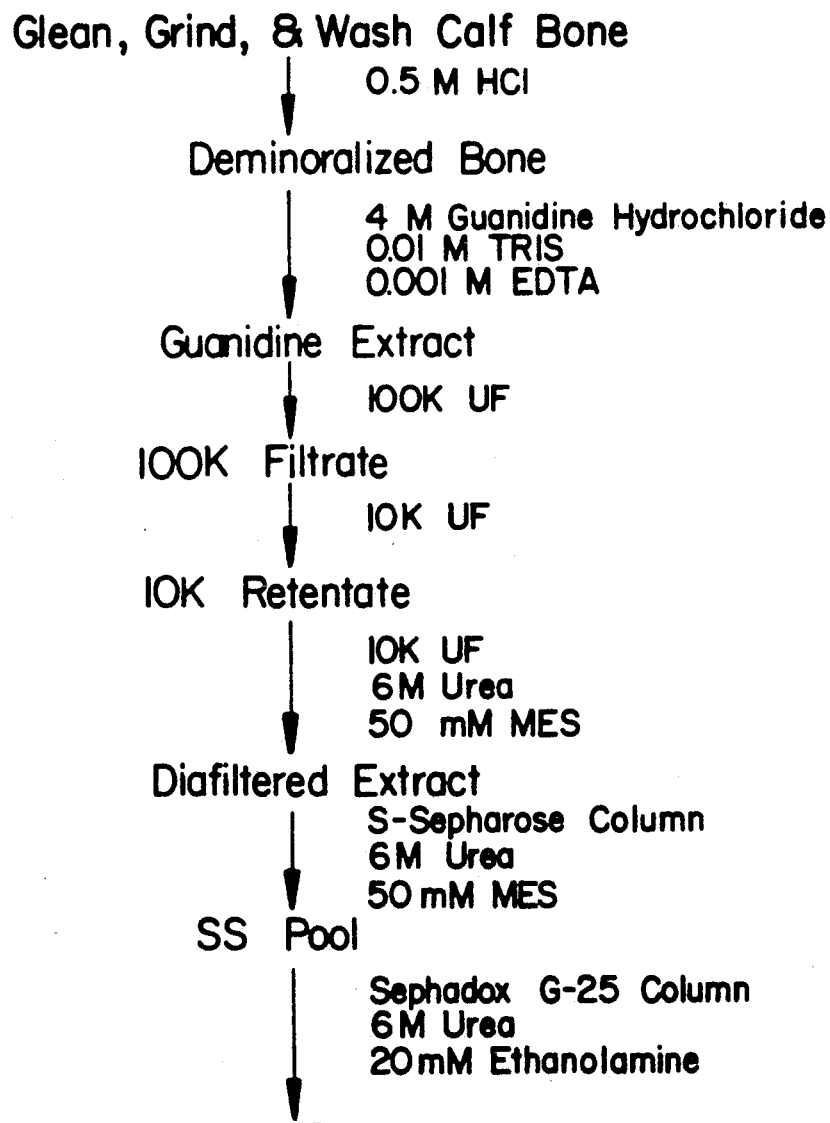
FIG. 9 illustrates an alternative method for the purification of P3 OF 31-34 (osteogenic factors) proteins from calf bone.

This example illustrates an alternative method providing the complete purification of the osteogenically active 31,000-34,000 dalton components of the P3 protein from larger quantities of bone powder and demonstrates that these protein components which are minor constituents of the P3 protein are osteogenically active in the essential absence of the major 22,000-24,000 dalton protein component. According to this example, bovine osteogenic factors were isolated from demineralized calf bone powder according to the procedure disclosed in FIG. 9. Approximately 200 pounds of diaphysial sections of calf bone were scraped clean of connective tissue and marrow was removed. The demarrowed sections were ground to a powder and washed with approximately 2100 liters of cold deionized water. The bone powder was allowed to settle during the water washes and the suspended connective tissue fragments were removed with the supernatant and discarded.

The bone powder was suspended in a total of approximately 570 liters of cold 0.5M HCl for about 2 hours and was then allowed to settle. The HCl was removed with the supernatant and discarded. The remaining HCl was removed by washing the bone powder with approximately 700 liters of cold deionized water, followed by approximately 350 liters of cold 0.1M Tris, pH 7, solution. The demineralized bone powder (demineralized bone) was allowed to settle and the supernatant was discarded.

The demineralized bone powder was suspended in approximayely 140 liters of cold 4M guanidine hychloride containing 0.01M Tris, pH 7,and 0.001M EDTA for about 20 hours. The extracted bone powder was removed by filtration and discarded. The supernatant (guanidine extract) was saved.

The guanidine extract was filtered through Amicon spiral cartridges with an average molecular weight cutoff of 100,000 daltons. The 100,000 dalton filtrate (100K filtrate) was then concentrated through Amicon spiral cartridges with molecular weight cutoffs of 10 000 daltons. The 10,000 dalton retentate (10K retentate) was saved and assayed for pH, conductivity, total protein content by BCA colorimetric protein assay (Pierce Chemicals, Rockford, Ill.), resolution of protein constitutents in the preparations using reducing SDS- PAGE followed by silver staining or coomassie blue staining and determination of the osteogenic activity using the rat implant assay disclosed below in Example 3.

The 10K retentate was exchanged into 6M urea containing 50 mM 2-(N-morpholino)ethanesulfonic acid (MES), pH 6.5, by diafiltration with an Amicon spiral cartridge with a molecular weight cutoff of 10,000 daltons.

The diafiltered extract was adjusted to a pH of 6.5 using 5M NaOH and a conductivity of 10 mS/cm using 5M NaCl and applied to a 0.4 liter S-Sepharose column (Pharmacia Chemicals, New Jersey) equilibrated with 6M urea containing 50 mM MES, pH 6.5, adjusted to conductivity of 10 mS/cm. The column was washed with 2.4 liters of 6.0M urea containing 50 mM MES, pH 6.5, adjusted to a conductivity of 10 mS/cm to elute the unbound proteins. The S-Sepharose active pool (SS Pool) was eluted with 1.2 liters of 6.0M urea containing 50 mM MES, pH 6.5, and 0.5M NaCl. The S-Sepharose active pool was concentrated using membrane filters with an average molecular weight cutoff of 10,000 daltons. The pH and conductivity of the preparation were determined, the total protein content was measured by BCA protein assay, the protein constituents were analyzed using SDS-PAGE followed by silver staining and the osteogenic activity was determined using the rat implant assay.

The S-Sepharose active pool was gel filtered with a 3 liter Sephadex G-25 column (Pharmacia Chemicals, N.J.) equilibrated with 6M urea containing 20 mM ethanolamine, pH 9.5. The first protein peak containing the active pool (G-25 Pool) was eluted with 3 liters of 6M urea containing 20 mM ethanolamine, pH 9.5.

The G-25 Pool was applied to a 0.7 liter Q-Sepharose column (Pharmacia Chemicals, N.J.) equilibrated with 6M urea containing 20 mM ethanolamine, pH 9.5. The column was eashed with 2.1 lites of 6M urea containing 20 mM ethanolamine, pH 9.5, to elute the unbound proteins. The osteogenically active protein pool (QS Pool) was eluted from Q-Sepharose column with 1.4 liters of 6M urea containing 20 mM ethanolamine, pH 9.5, and 0.2M NaCl. The QS Pool was adjusted to a pH of 6-7 with glacial acetic acid and concentrated using membrane filters with an approximate molecular weight cutoff of 10,000 daltons. The QS Pool was assayed for pH and conductivity; the total protein content was determined by BCA protein assay, the protein constituents were analyzed by reducing SDS-PAGE followed by silver staining and the osteogenic activity was measured using the rat implant assay.

The QS Pool was then applied to a preparative C-18 HPLC column equilibrated with a buffer containing, by volume, 70% Buffer A (Buffer A is 0.05% trifluoroacetic acid in water) and 30% Buffer B (Buffer B is 0.025% trifluoroacetic acid in acetonitrile). Bound proteins were eluted using a linear gradient of 30% to 60% acetonitrile in 120 minutes. As previously characterized for P3 protein of example 1, the osteogenic activity (Prep HPLC Pool) eluted within the concentrations of 35% to 45% acetonitrile. The Prep HPLC Pool was lyophilized and resuspended in 1 ml of water. The Prep HPLC Pool was assayed for pH and conductivity; the total protein content was determined by BCA protein assay, the protein constituents were analyzed by reducing SDS-PAGE followed by silver staining and the osteogenic activity was measured using the rat implant assay.

The Prep HPLC Pool was adjusted to a protein concentration of 0.5 mg/ml in 6M urea containing 50 mM Tris, pH 7.5-8.0, 20 mM ethanolamine and 0.5M NaCl and was applied to a 5-10 ml Chelating Sepharose 6B column (Pharmacia Chemicals, New Jersey) charged with Cu 2+ and equilibrated with 6M urea containing 50 mM Tris, pH 7.5-8.0, 20 mM ethanolamine and 0.5M NaCl. The column was washed with 5 column volumes of equilibration buffer followed by 10 column volumes of 6M urea containing 50 mM Tris, pH 7.4-7.8, to elute the unbound proteins. Bound proteins were eluted with 10 column volumes of 6M urea containing 50 mM Tris, pH 7.4-7.8, and 4 mM imidazole. The osteogenic activity (CC Pool) was eluted from the copper chelate column with 10 column volumes of 6M urea containing 50 mM Tris, pH 7.4-7.8, and 15 mM imidazole. The CC Pool was assayed for total protein as estimated by absorbence at 280 nm, and its osteogenic activity was measured using the rat implant assay.

The CC Pool was adjusted to 25% ammonium sulfate and loaded onto a 1-3 ml column of Phenyl-Sepharose (Pharmacia Chemicals, N.J.) equilibrated with 6M urea containing 25% ammonium sulfate, 50 mM Tris pH 7.4-7.8. The column was washed with 10 column volumes of 6M urea containing 25% ammonium sulfate, and 50 mM Tris pH 7.4-7.8, to elute the unbound proteins. Bound proteins were eluted with 10 column volumes of 6M urea containing 15% ammonium sulfate, 50 mM Tris pH 7.4-7.8. The osteogenic activity (PS Pool) was eluted from the Phenyl-Sepharose column with 6M urea containing 50 mM Tris pH 7.4-7.8, was assayed for total protein as estimated by absorbence at 280 nm, and its osteogenic activity was measured using the rat implant assay.

The PS Pool was applied to a semi-preparative or analytical C-18 HPLC column equilibrated with a buffer containing, by volume, 70% Buffer A and 30% Buffer B, as described previously (Buffer A is 0.05% trifluoroacetic acid in water and Buffer B is 0.025% trifluoroacetic acid in acetonitrile). Bound proteins were eluted using a linear gradient of 30% to 60% acetonitrile. As was previously characterized, the osteogenic activity (HPLC Pool) eluted within the concentrations of 35% to 45% acetonitrile. The HPLC Pool was assayed for total protein as estimated by absorbence at 229 nm and its osteogenic activity was measured using the rat implant assay.

Characterization of Bovine Osteogenic Factors

In the following examples, preparations of bovine osteogenic factors were characterized according to various procedures.

EXAMPLE 3

Biological Activity

The induction of bone matrix was measured using a rat implant assay as generally described by Sen, Walker and Einarson, 1986. In *Development and Diseases of Cartilage and Bone Matrix*, eds. A. Sen and T. Thornhill, pp. 201-220. Alan R. Liss, New York and Sampath and Reddi, *Proc. Natl. Acad. Sci. U.S.A.*, 80:6591-6595 (1983). Approximately 70-100 mg of inactive bone matrix (bone collagen) was mixed with an aqueous solution of osteogenic protein preparation and the water removed by lyophilization. The dried coated granules were packed in gelatin capsules (Eli Lilly #5) and each capsule was subcutaneously implanted near the thigh muscles in each back leg of male Long Evans rats. The implanted rats were sacrificed 21 to 28 days following implantation and the implant tissue was surgically removed and placed in Bouin's Solution. The specimens were then decalcified and processed for toluidine blue stained sections. Histomorphology and percent ossification was determined by examination of the stained sections. Potency is defined by the amount of protein (mg) required for implantation with inactive bone matrix yielding at least 10% of the area of the stained sections occupied by osteoid activity.

TABLE 3

Purification of Osteogenic Factors

| Sample | Total Protein | Potency in Rat (mg/implant) |
|---|---|---|
| Guanidine Extract | 130,000–170,000 mg | |
| 10K Retentate | 6,000–15,000 mg | 10.0 |
| S-S Pool | 300–900 mg | 1.0 |
| QS Pool | 70–250 mg | 0.25 |
| Prep HPLC Active Pool | 4–12 mg | 0.05 |
| CC Pool | 2–5 mg | 0.025 |
| PS Pool | 0.5–1 mg | 0.01 |
| HPLC Active Pool | 0.01–0.05 mg | 0.001 |

The increase in potency of the various osteogenically active protein preparations obtained using purification steps according to Example 2 is shown in Table 3, above, with the HPLC Active Pool having a potency of 0.001 mg/implant which is significantly higher than the P3 protein produced according to Example 1.

EXAMPLE 4

Estimation of Molecular Weight of Osteogenic Activity

Osteogenically active protein preparations, obtained using various purification steps described in Example 2, were suspended in SDS sample dilution buffer (in the absence of reducing reagents) and applied to a 10% SDS polyacrylamide gel and electrophoresed. Molecular weights were determined relative to either prestained molecular weight standards (Bethesda Research Labs, Gaithersburg, Md.) or non-prestained molecular weight standards (Bio-Rad, Richmond, Calif.). After completion, the gel lanes were sliced into pieces. Each piece was electroeluted to extract the protein. The eluted protein was precipitated with acetone, resuspended in guanidine hydrochloride, dialyzed against water, lyophilized onto inactive bone matrix and implanted into rats to assay osteogenic activity according to Example 3. In this gel system, the osteogenic activity was eluted from gel slices corresponding to the apparent molecular weight range of 28,000–34,000 daltons.

EXAMPLE 5

Molecular Weight of Purified Osteogenic Factors

Purified osteogenically active protein preparation as obtained in the HPLC Active Pool of Example 2 were suspended in S the absence of reducing reagents (−DTT), electrophoresed on 12.5% or 15% SDS polyacrylamide gels and the protein bands visualized by silver staining. Molecular weights are determined relative to non-prestained molecular weight standards (Bio-Rad). This gel system revealed that the HPLC Active Pool contained protein bands which migrate within the molecular weight range of 31,000–34,000 daltons (see FIG. 10A).

EXAMPLE 6

Determination of Molecular Weights of Purified Osteogenic Factors Under Reducing Conditions and Purification of Reduced Subunits Purified osteogenically active proteins in the HPLC Active Pool were subjected to an alternative analytical method whereby protein subunits held together by disulfide bonds can be resolved by reduction of these bonds in SDS dilution buffer in the presence of a reducing agent (dithiothreitol or β-mercaptoethanol) and electrophoreses on 12.5% or 15% SDS polyacrylamide gels. Molecular weights were determined relative to non-prestained molecular weight standards (Bio-Rad). In this gel system, the HPLC Active Pool revealed proteins migrating as two broad bands within the molecular weight ranges of 16,000–17,500 and 17,500–19,000 daltons (see FIG. 10B).

The HPLC Active Pool was made 6M in guanidine hydrochloride, 50 mM in ethanolamine and 50 mM in dithiothreitol to reduce the disulfide bonds. The reduced sample was diluted at least 2 fold with either water or 0.05% trifluoroacetic acid in water and loaded onto an analytical C-18 HPLC column equilibrated with a buffer comprising, by volume, 70% Buffer A and 30% Buffer B, as described previously (Buffer A is 0.05% trifluoroacetic acid in water and Buffer B is 0.025% trifluoroacetic acid in acetonitrile). Bound proteins were eluted using a linear gradient of 30% to 60% acetonitrile in 60 minutes. Four prominent peaks of protein, designated A, B, C and D, were detected by monitoring UV absorbence at 229 nm; these eluted within the concentrations of 40% to 47% acetonitrile (see FIG. 11A). When analyzed by reducing SDS gel electrophoresis followed by silver staining, the reduced subunit A migrated within the molecular weight range of 17,500–19,000 daltons, the reduced subunit B migrated within the molecular weight range of 16,000–17,500, the reduced subunit C migrated within the molecular weight range of 17,500–19,000 and the reduced subunit D migrated within the molecular weight range of 17,500–19,000 (see FIG. 11B).

EXAMPLE 7

Amino Acid Sequences of Bovine Osteogenically Active Proteins P3 OF 31- 34

The isolated reduced subunits purified from HPLC Active Pool as disclosed in Example 6, were analyzed by a gas phase sequenator (Applied Biosystems, Model 470A), and found to have the following amino-terminal sequences:
Subunit A: SAPGRRRQQARNRSTPAQDV
Subunit C: SXKHXXQRXRKKNNN
Subunit D: STGGKQRSQNRSKTPKNQEA
where the amino acids are represented by the well known one-letter and three-letter designations presented in Table 4 below.

TABLE 4

| Amino Acid | Three-Letter Abbreviation | One-Letter Symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic acid | Glu | E |

TABLE 4-continued

| Amino Acid | Three-Letter Abbreviation | One-Letter Symbol |
|---|---|---|
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Undetermined |  | X |

The isolated subunit B yielded no detectable amino-terminal sequence. When subunit B was digested with Staph V8 protease, and rechromatographed by HPLC, two detectable internal fragments were isolated having the following amino acid sequences:

| Subunit B: | XVVLKNYQDMV |
|---|---|
|  | XEKVVLKNYQDM | where X represents an unassigned amino acid.

EXAMPLE 8

Osteogenic Compositions for Implantation

The osteogenic preparations of the invention may be used to prepare osteogenic compositions for implantation into mammals. The Prep HPLC Pool of Example 2 may be admixed with one or more of a variety of physiologically acceptable matrices. Such matrices may be resorbable, non-resorbable or partially resorbable. Resorbable matrices include polylactic acid polycaprolactic acid, polyglycolic acid, collagen, plaster of paris and a variety of thermoplastic polymer materials. Non-resorbable materials include hydroxyapatite and partially resorbable materials include matrices such as tricalcium phosphate. The Prep HPLC Active Pool may be adsorbed onto the matrix material which can be either in a granular or solid form. The osteogenic composition may then be dried by lyophilization.

EXAMPLE 9

Device Coated With Osteogenic Preparations

In this example, the Prep HPLC Active Pool of Example 2 containing the osteogenically active proteins was used to form osteogenically active devices useful for the healing of bone defects. The devices were prepared by absorbing the Prep HPLC Active Pool onto solid delivery matrices comprising either a porous hydroxyapatite disc (Interpore 200, Interpore International, Irvine, Calif.) or a porous polylactic acid disc (DRILAC, OSMED Incorporated, Costa Mesa, Calif.). The discs were 8 to 10 mm in diameter and 3 mm thick and were coated with 0.2 to 0.3 mg of the Prep HPLC Active Pool which was dried onto the matrices by lyophilization. The device may then be sterilized by gamma-irradiation with as much as 3.3 to 3.5M rads or other suitable means. The devices comprising the osteogenic preparation and the matrix were implanted into trephine defects created in New Zealand Albino Female rabbits, weighing 2.5 to 3.0 kg. Specifically, test devices either coated with the osteogenic preparation or not coated with the osteogenic preparation were surgically implanted into the calvaria using appropriate aseptic surgical techniques. Animals were anesthetized with an intramuscular injection of Ketamine and Xylazine. Following a midline incision, the calvarium was exposed and two trephine holes (one on each side of the midline) 5 mm posterior to the orbits, 8–10 mm in diameter and to the depth of the dura were cut into the calvarium. Trephine defects were created using a Stille cranial drill, exercising great care not to injure the dura. A test device was implanted into one trephine hole while the trephine hole on the opposite side was left empty. Following surgical implantation, antibiotic prophylaxis with penicillin and streptomycin was administered. The animals were followed daily by clinical observations. At explant, the calvaria was removed en block. The specimens were fixed in 10% buffered formalin, decalcified and processed for hematoxylin and eosin stained sections. Histomorphology and qualitative determination of percent ossification was determined by examination of the stained sections (see Table 5 below). The percent area of activity is estimated by eye from the fields of view, or fraction of fields of view, of newly formed bone matrix as compared to the total fields of view not occupied by the matrix in the entire full cross section.

TABLE 5

% Ossification in Devices Implanted into Rabbit Trephine Defects

| Test Device | Time of Explant | |
|---|---|---|
|  | 6 weeks | 12 weeks |
| Uncoated Hydroxyapatite | <10% | <25% |
| Uncoated Polylactic Acid | <10% | <10% |
| Hydroxyapatite Coated with Osteogenic Preparation | >90% | >90% |
| Polylactic Acid Coated with Osteogenic Preparation | >90% | >90% |
| Hydroxyapatite Coated with Osteogenic Preparation and Treated with Gamma-Irradiation | >75% | >90% |

EXAMPLE 10

Amino Acid Sequences of CNBr Fragments of P3 OF 31-34

The isolated reduced subunits purified from HPLC Active Pool (Example 6) were adsorbed onto polyvinylidine difloride (PVDF) transfer membrane (Millipore, Bedford, Mass.), exposed to vapors from 80 mg/ml CNBr in 70% formic acid for 15 to 20 hours and sequenced using the gas phase sequenator. The following amino acid sequences are represented by the well-known one-letter designations presented in Table 4.

Subunit A, following cleavage with CNBr, yielded sequences from the simultaneous sequencing of several fragments corresponding to the amino terminal sequence described in Example 7:
ANt: SAPGRRRQQARNRSTPAQDV
and an internal fragment:
A1: NPEYVPK Subunit B, following cleavage with CNBr, yielded sequences from the simultaneous sequencing of two internal fragments:
B1: LYLDENEK
B2: VVEGXGXR
When compared with the sequences of fragments of subunit B cleaved with staph V8 protease (Example 7), fragments B1 and B2 contain overlapping regions, allowing an extended internal sequence in subunit B:

| | |
|---|---|
| B1: | LYLDENEK |
| Staph V8: | XEKVVLKNYQDM |
| Staph V8: | XVVLKNYQDMV |
| B2: | VVEGXGXR |
| Consensus: | LYLDENEKVVLKNYQDMVVEGXGXR |

Subunit D, following cleavage with CNBr, yielded sequences from the simultaneous sequencing of several fragments corresponding to the amino terminal sequence described in Example 7:
DNt: STGGKQRSQNRSKTPKNQEA
and an internal sequence:
D1: XATNHAIVQTLVHFIN The isolated reduced subunit C, purified from the HPLC Active Pool (Example 6), was adsorbed onto a PVDF transfer membrane, subjected to 20 cycles of amino terminal sequencing using the gas phase sequenator, subjected to cleavage by CNBr vapors, and then sequenced using the gas phase sequenator. Subunit C, following cleavage with CNBr, yeilded the following internal sequence:
C1: LYLXEYDXVVLXNYQ The amino terminal and internal sequences of subunits A, B, C ad D derived from bovine bone can be aligned with homologous regions from the deduced amino acid sequences of cDNA clones encoding the polypeptides designated BMP-2A, BMP-2B and Bgr-1 (FIG. 12). Homologous regions for the deduced sequences of BMP-2A, BMP-2B (Wozney, et al., Science, 242, 1528–1534 (1988)) and Vgr-1 (Lyons, et al., Proc. Natl. Acad. Sci. USA, 86, 4554–4558 (1989)) are boxed. Homologous residues in the sequences for bovine subunits A, B, C and D, as compared to the deduced sequences for BMP-2A, BMP-2B and Vgr-1, are bold-faced. Comparison of the similarities and differences of the sequences of subunits B and C and the sequences of BMP-2A and BMP-2B indicate that bovine subunit B shares the same sequence as BMP-2A while bovine subunit C shares the same sequence as BMP-2B.

EXAMPLE 11

Subunit Compositions of Purified Osteogenically Active Proteins P3 OF 31-34

Figure 13A:
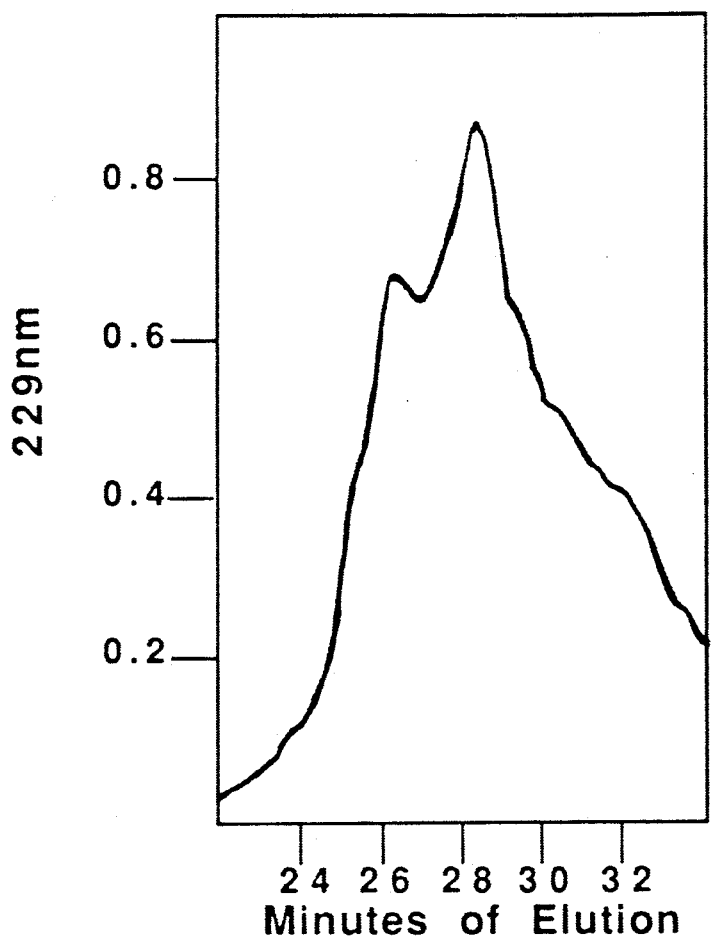
FIG. 13A represents the elution profile obtained by high performance liquid chromatography, on a reverse phase, C18, column, of the PS Pool.
Figure 13B:
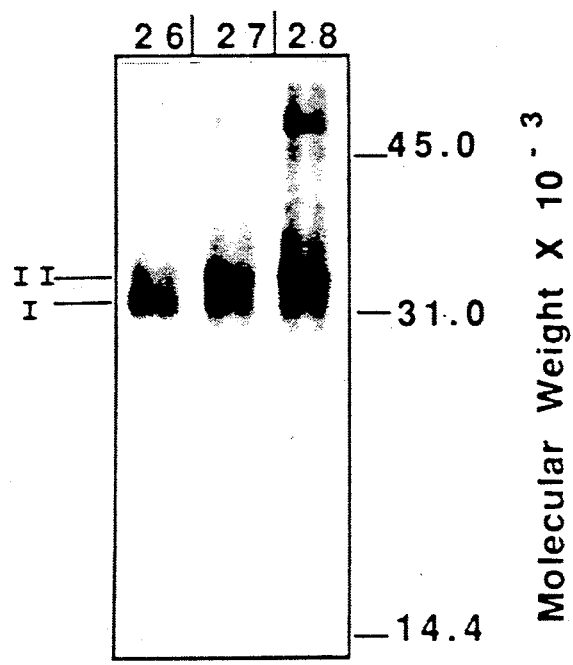
FIG. 13B shows non-reducing SDS polyacrylamide gel electrophoresis of P3 OF 31-34 proteins eluting in fractions 26, 27 and 28 from the reverse phase HPLC of the PS Pool.

Individual fractions, eluting within the HPLC active pool (Example 5) and containing the osteogenically active proteins P3 OF 31-34 (FIG. 13A), were analyzed by SDS polyacrylamide gel electrophoresis in the absence of reducing reagents (FIG. 13B). FIG. 13A shows the elution profile obtained by high performance liquid chromatography, on a reverse phase C18 column of the PS Pool. FIG. 13B shows non-reducing SDS polyacrylamide gel electrophoresis of P3 OF 31-34 proteins eluting in fractions 26, 27 and 28 from the reverse phase HPLC of the PS Pool. These individual fractions were further analyzed (as described in Example 6) by reduction of the disulfide bonds with 50 mM-dithiothreitol in 50 mM ethanolamine and 6M guanidine hydrochloride and chromatography on a C18 HPLC column (FIG. 14). FIG. 14A shows the isolation and identification of subunits of the P3 OF 31-34 proteins eluting in fraction 26 from the reverse phase HPLC of the PS Pool, while FIG. 14B shows the isolation and identification of P3 OF 31-34 proteins eluting in fraction 28. Subunits A, B, C and D are designated by the solid lines in the figures. Fraction 26, the sample comprising the lowermost band of the P3 OF 31-34 region (Band I of FIG. 13B), was found to contain predominantly subunits B and D with smaller amounts of subunits A and C. Fraction 28, the sample comprising predominantly the uppermost band of the P3 OF 31-34 region (Band II of FIG. 13B), together with a smaller amount of Band I, was found to contain increased amounts of subunits A and C, and a decreased amount of subunit D, as compared to the relative amount of subunit B.

These individual fractions, eluting within the HPLC active pool and containing the osteogenically active proteins P3 OF 31- 34, were electrophoresed on 12.5% SDS polyacrylamide gels in the absence of reducing reagent (−DTT), electrophoretically transferred to polyvinylidine difloride (PVDF) transfer membranes in the presence of 10% methanol, 10 mM cyclohexylamino-1-propanesulfonic acid, pH 10-11, at 0.5 amp for 15 to 30 minutes, and visualized by staining with Coomassie brilliant blue R250. Individual protein bands in the region of P3 OF 31-34, defined here as Band I (lower) and Band II (upper), were sliced from the membrane and subjected first to N-terminal sequencing, and then to internal sequencing following treatment with CNBr as described in Example 10. These procedures revealed the following sequence for Bands I and II:

| Band Sequenced | Sequences | Subunit Identity |
|---|---|---|
| Band I Internal | XATNXAIVQTL | D |
| | LYLDEXEXVVL | B |
| Band II N-Terminal | XXXGRRXQ | A |
| | XXGGXQR | D |
| Band II Internal | LYLDXNXXVVLXN | B |
| | XPEXVPX | A | where the amino acids are represented by the well-known one-letter designations presented in Table 4.

These results indicated that Band I, the lowermost band of the P3 OF 31-34 proteins, contains predominantly subunits D and B, and that Band II, the uppermost and of the P3 OF 31-34 proteins, contains predominantly subunits A and B. These compositions, as well as the observation that these subunits are purified as disulfide-linked dimers in the purified P3 OF 31-34 proteins (Examples 5 and 6), indicate that subunits A subunits D and B may be disulfide-linked as another heterodimer.

EXAMPLE 12

Osteogenically Active Proteins P3 OF 31-34

Antisera specific for proteins containing subunits A or D were generated against the following synthetic peptides obtained from Peninsula Laboratories, Belmont, Calif.:

| Antigen | Antibody Designation |
|---|---|
| Subunit A (SAPGRRRQQARNRSTPAQDV)$_8$lys$_7$ | AbANt |
| Subunit D (STGGKRRSQNRSKTPKNQEA)$_8$lys$_7$ | AbDNt |

Antisera were generated in rabbits (3- to 6-month-old New Zealand white male) using standard procedures of subcutaneous injections, first in complete Freunds adjuvant, and later (at 14 and 21 days) in incomplete Freunds adjuvant followed by bleeding and preparation of antisera.

The AbANt and AbDNt antisera were cross-reactive with the synthetic peptide antigens when used in an ELISA or Dot Blot format and the reduced subunits A and D when used in a Western Blot format. The AbANt and AbDNt antisera were also cross-reactive with the osteogenically active proteins P3 OF 31-34 when used in either an ELISA, Western or Dot Blot format. These antisera are not cross-reactive with any presently defined form of subunit B or subunit C as determined by Western Blot and Dot Blot analysis as against purified subunit B and subunit C.

EXAMPLE 13

Presence of P3 OF 31-34 Proteins in P3

The protein contained in P3 was isolated substantially as described in Example 1 and FIGS. 2 and 3, and was purified utilizing gel filtration on Sepharose S-200 and reverse-phase HPLC on a Protesil 300 octyl column equilibrated in 0.1% TFA and 10% ACN. The protein was then suspended in a SDS dilution buffer in the presence of reducing agents (+DTT) and electrophoresed on 12.5 or 15% SDS polyacrylamide gels (SDS-PAGE). Proteins contained within the gel were visulaized using Coomassie brilliant blue, or were electrophoretically transferred to nitrocellulose in the presence of 10% methanol, 10 mM cyclohexylamino-1-propanesulfonic acid (CAPS), pH 10-11, at 0.5 amp for 15 to 30 minutes. The nitrocellulose filter was treated for Western Blot analysis utilizing antibodies generated agaisnt synthetic peptide of the N terminal sequences of subunit A (AbANt) and subunit D (AbDNt).

The nitrocellulose paper containing the protein was placed in a solution-designated buffer P (composed of 20 mM phosphate, pH 7.4; 0.15M NaCl; 0.05% Tween-20; 0.25% gelatin; and 0.02% sodium azide) for a minimum of 1 hour at 22° C. with agitation.

Buffer P was then replaced by buffer Q (composed of buffer P plus antibodies AbANt and AbDNt) for a minimum of one hour at 22° C. (or overnight at 4° C.). Buffer Q was replaced by Buffer P, which was changed four times over a minimum of one hour. Buffer P was replaced by Buffer R (buffer P plus 125I protein A at 2.5 x $10^5$ cpm/ml, Amersham) and incubated for one hour at 22° C. with agitation. Buffer R was replaced by Buffer P, which was changed at least four times during one hour of incubation.

Figure 15:
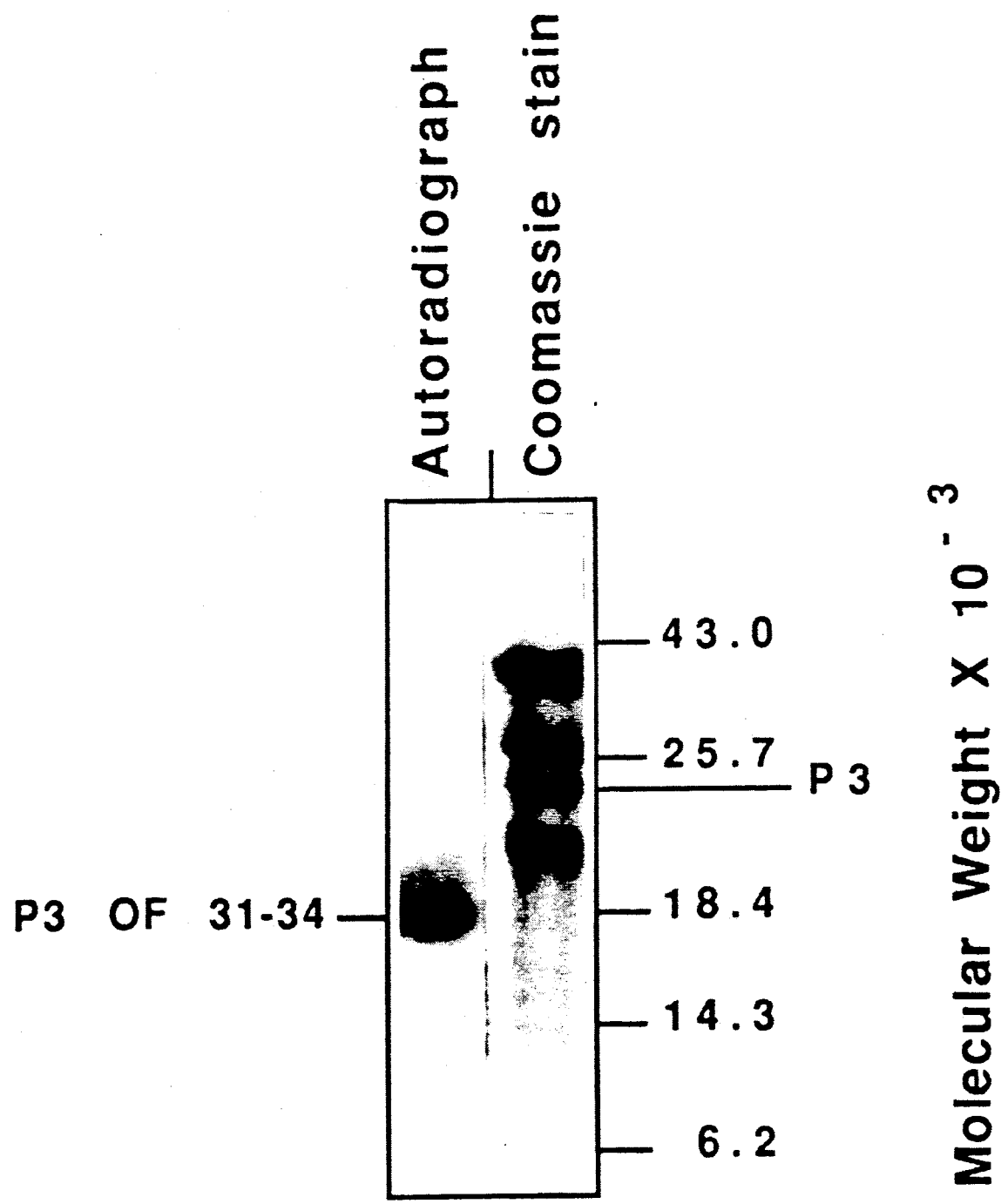
FIG. 15 shows reducing SDS polyacrylamide gel electrophoresis of P3 and P3 OF 31-34 proteins isolated and visualized using either Coomassie stain, or autoradiography following Western Blot analysis utilizing antibodies generated against synthetic peptides of the N terminal sequences of subunit A (AbANt) and subunit D (AbDNt).

The moist nitrocellulose filter was placed between sheets of plastic wrap, and together with a lighting screen and X-ray film (Dupont Cronex, Wilmington, Del.), enclosed in a light-proof folder, and placed at −70° C. for an appropriate period of time. The exposed film was developed using standard techniques and equipment, and the resulting autoradiograph shown in FIG. 15 demonstrates the presence of subunits A and/or D within the P3 fraction.

EXAMPLE 14

Glycosylation of Bovine Osteogenically Active Protein P3 OF 31-34

Reduced subunits A and D were purified from HPLC active pool as disclosed in Example 6 and were subjected to digestion by Peptide-N4 (N-acetyl-beta-glucosaminyl) arginine amidase (N-glycanase, Genzyme) and endo-beta-N-acetyl glucosaminidase H (endo H, Genzyme) according to manufacturer's specifications. The relative molecular weights of the reduced subunits, both before and after digestion with the endoglycosidases, was evaluated by electrophoresis on a 15% SDS polyacrylamide gel, followed by Western analysis using the antibodies designated as AbANt and AbDNt. FIG. 16 shows reducing SDS polyacrylamide gel electrophoresis of reduced subunits A and D and after treatment with either endo H or N-glycanase. Western Blot analysis of isolated reduced subunit A, both before and after treatment with glycosidases, is shown in panel A. Western Blot analysis of isolated reduced subunit D, both before and after treatment with glycosidases, is shown in panel D. A decrease in the relative molecular weights, from approximately 17,500–19,000 daltons to 14,000–16,000 daltons, of each of the digested subunits A and D, indicated that the subunits A and D contain asparagine-linked carbohydrate which was sensitive to digestion either by endo H or N-glycanase.

EXAMPLE 15

Identification of Sequences of Human cDNA Encoding Proteins Homologous to Subunit D of Bovine Osteogenically Active Proteins P3 OF 31-34

A variety of techniques can be used to identify sequences of human DNA encoding proteins homologous to a particular sequenced protein. Such methods include the screening of human DNA, human genomic libraries and human cDNA libraries. A variety of oligonucleotide probes can be used including probes exactly complementary to the human DNA sequence, mixtures of probes complementary to all or some of the possible DNA sequences coding for the particular protein sequence, degenerate probes synthesized such that all possible sequences complementary to all possible DNA sequences coding for the particular protein sequence are represented, and degenerate probes synthesized using nucleotide analogues such as deoxyinosine triphosphate. In this example, the polymerase chain reaction (PCR) technique was used to amplify sequences of human cDNA encoding proteins homologous to subunit D of bovine osteogenically active proteins P3 OF 31-34.

Preparation of cDNA from U-2 OS Cells

The human osteogenic sarcoma cell line U-2 OS was obtained from the ATCC (American Type Culture Collection, Rockville, Md.) and maintained in McCoy's 5a medium supplemented with 10% fetal calf serum and 1% glutamine/penicillin/streptomycin. Unless otherwise described, DNA manipulations, definition of terms, and compositions of buffers and solutions are described by Maniatis, T., et al., *Molecular Cloning*: A Laboratory Manual (1982). Poly (A)+RNA was isolated from U-2 0S cells using the Fast Track-mRNA isolation kit from Invitrogen (San Diego, Calif.). A first strand cDNA copy of the mRNA was generated with oligo (dT) as the primer using the AMV Reverse Transcriptase System I from Bethesda Research Laboratories (BRL, Gaithersburg, Md.). Each reaction used 1 μg of poly (A)+RNA which was reverse transcribed into first strand cDNA that was used as template in eight separate polymerase chain reaction (PCR) DNA amplification reactions. Following cDNA synthesis, RNA was hydrolyzed by treatment with 50 mM NaOH at 65° C., followed by neutralization in 0.2N HCl.

PCR Amplification

Polymerase chain reaction (PCR), as described by R. K. Saiki, et al., Science 239:487-491 (1988), was used to amplify DNA from U-2 OS cDNA prepared as described above. Oligonucleotide primers for PCR were synthesized on an automated DNA synthesizer and were derived from the amino terminal and internal amino acid sequences of bovine subunit D. The 5' PCR primer, designated ODM-1, corresponded to sequence from the first 11 amino acids from the amino terminus of bovine subunit D, namely STGGKQRSQNR. This 32-mer contained all possible combinations of nucleotide sequence coding for this sequence of amino acids and was greater than 4-million-fold degenerate. The nucleotide sequence of ODM-1 was 5'-[T/A][C/G]NACNGGNGGNAA[G/A]CA[G/A][C/A]GN[T/A][C/G]NCA[G/A]AA[C/T][C/A]G-3'. Bracketed nucletides are alternatives, and "N" means all alternatives (A, C, T and G).

The 3' PCR primer corresponded to an internal sequence of bovine subunit D, namely, NHAIVQTLVHFIN, and was synthesized as the inverse and complementary sequence. This oligonucleotide primer was designated ODB-1 and had the sequence 5'-TTTTTTTTGGATCC[G/A]TTXAT [G/A]AA[G/A]TGXACXA[G/A]XGT[C/T]TGXACX-ATXGC[G/A]TG[G/A]T T-3'. Bracketed nucleotides are alternatives, and "X" represents the nucleotide analog deoxyinosinetriphosphate (dITP), which was used in all positions where all four of the nucleotides (A, C, T or G) were possible The sequence is preceded on the 5' end by a string of eight T's, followed by the sequence GGATCC which designates a BamHI recognition site, leaving a stretch of 39 nucleotides corresponding to the internal amino acid sequence of bovine subunit D.

Amplification of DNA sequences coding proteins homologous to bovine subunit D using these two primers was accomplished using the Perkin-Elmer Cetus Gene Amp DNA Amplification Reagent Kit (obtained either from Perkin-Elmer Cetus, Norwalk, Conn., or United States Biochemical Corporation, Cleveland, Ohio). The PCR reaction contained 1 μg of each primer ODM-1 and ODB-1, ⅛ of the synthesized U-2 OS first strand cDNA (approximately 25-50 ng), 200 μM of each dNTP, and 2.5U Ampli-Tag DNA Polymerase in the kit-supplied reaction buffer of 50 mM KCl, 1.5 mM MgCl$_2$, 0.1% (w/v) gelatin. PCR was performed for 30 cycles consisting of 1.5 minutes denaturation at 94° C., 2 minutes annealing at 50° C. and 3 minutes elongation at 72° C. After the 30 cycles, a final 10-minute elongation at 72° C. is performed.

The PCR products were analyzed by agarose gel electrophoresis, which revealed a major band of amplified DNA of approximately 300 bp. A Southern Blot was performed in which the DNA in the gel was transferred to a Nytran nylon membrane (Schleicher and Schuell, Keene, NH) using an LKB Vacugene Vacuum Blotting Unit, and then the DNA was UV-crosslinked to the membrane using a Stratalinker (Stratagene, La Jolla, Calif.). The membrane was probed for amplified sequences encoding proteins homologous to bovine subunit D using a probe corresponding to the amino acid sequence KTPKNQEALR. This sequence is found near the amino terminus of bovine subun:t D, following the sequence used to constructed the 5' PCR primer. This probe would therefore hybridize to amplified sequences that encode proteins homologous to bovine subunit D without overlapping either of the two primers used in the amplification. This 29-mer probe was designated ODibb and had the sequence AAX-ACXCCXAA[G/A]AA[C/T]CAXGA[G/A] GCX[C/T]TX[C/A]G, where bracketed nucleotides are alternatives and "X" represents dITP, which was used in positions where all four nucleotides (A, C, T or G) were possible. The Southern Blot was prehybridized at 42° C. in 5xSSPE, 0.5% SDS, 3× Denhardt's, 100 μg/ml salmon sperm DNA, then hybridized at 42° C. in 6xSSPE, 0.5% SDS to the ODibb probe which had been radioactively labelled using polynucleotide kinase and γ[$^{32}$P]ATP. The blot was washed at 42° C. in 2xSSC, 0.1% SDS. Autoradiography of the blot showed that ODibb hybridized specifically to the 300-bp PCR-amplified DNA.

EXAMPLE 16

Cloning and Sequencing of Human cDNA's Encoding Proteins Homologous to Subunit D of Bovine OF 31-34

5' phosphates were added to the blunt-ended PCR product of Example 15 using kinase and ATP, and the DNA was then ligated into the SmaI cut (blunt end) site of the vector pT7T3 18U (Pharmacia, Piscataway, N.J.). Following digestion with SmaI to linearize any religated vector, the recombinant plasmid DNA was used to transform *E. coli* TG1 cells. Several transformants were picked and used to purify plasmid DNA by a mini-lysate procedure. The size of the insert contained in these plasmids was confirmed to be 300 bp by restriction analysis.

DNAs from seven different transformants were sequenced by dideoxy sequencing methods (Sequenase, United States Biochemical Corp). The sequences of three of these clones were identical to each other and, when translated to amino acid sequence, it was confirmed that they were homologous to the sequence of bovine subunit D. The sequence of the PCR-amplified DNA, designated "hOD," is shown in FIG. 17, along with the known and derived amino acid sequences. Only the DNA sequence between the two primers is shown, since the degeneracy of the primers did not allow the identification of the exact sequence in these regions. The sequence of the first 34 amplified nucleotides following the ODM-1 primer codes for amino acid sequence previously identified in bovine subunit D.

The sequences of the other four recombinant clones, while identical to each other, were different from the hOD-amplified sequence and encoded a different sequence of amino acids. This family of clones was designated "hOE," and its sequence is shown in FIG. 18. FIG. 19 shows the homology between hOD and hOE-amplified sequences, indicating 69-70% identity at both the nucleotide and amino acid level in this region. FIG. 19A shows the homology between the derived amino acid sequences of the PCR-amplified hOD and hOE sequences wherein the homologous residues are boldfaced. In the region following the first cysteine residue, these two sequences share 39/44 identical amino acids, a highly conserved region among the members of the TGF-β family. FIG. 19B shows the homology between the nucleotide sequences of the PCR-amplified sequences designated hOD and hOE.

EXAMPLE 17

Recombinant Expression of P3 OF 31-34 Subunits

Complete and partial P3 OF 31-34 subunit polypeptide products and analogs may be prepared utilizing recombinant DNA molecules in bacteria, yeast or mammalian expression systems. DNA encoding products based on amino acid sequences derived from isolated P3 OF 31-34 subunits according to the present invention can be inserted into an expression vector, for example, a plasmid, phage or viral expression vector [Vieira, et al., *Gene*, 19, 259-268 (1982); Young, et al., *Proc. Natl. Acad. Sci. (USA)*, 80, 1194-1198 (1983); Bitter, et al., *Gene*, 32, 263-274 (1984); Cepko, et al., *Cell*, 37, 1053-1062 (1984); and Gorman, et al., *Mol. Cell. Biol.*, 2, 1044-1051 (1982)].

In particular, P3 OF 31-34 subunits D and E may be produced by expression of DNA characterized by nucleotide sequences set out in FIGS. 17 and 18, respectively. Alternatively, DNA characterized by nucleotide sequences encoding the same sequence of amino acids as set out in FIGS. 17 and 18 could be inserted into an expression vector for the same purpose. Analogs of these subunits could also be prepared by means of DNA sequences which hybridize (or which would hybridize but for the redundancy of the genetic code) with at least 80% of the nucleotide sequence shown in FIGS. 17 and 18.

Another aspect of applicants' invention involves the preparation of osteogenic materials comprising dimers of subunit D and heterodimers of subunit D and subunit B. Osteogenically active dimers can be produced either by expression of nucleic acid sequences encoding subunit D and subunit B in the same cell allowing disulfide bonds to form during the biosynthetic process, or by separately expressing each subunit in different cells and then combining each expressed subunit in such a way as to form a disulfide linked dimer. Dimers of subunit A and heterodimers of subunit A and subunit B could similarly be prepared. Osteogenic preparations comprising recombinant produced dimers and heterodimers could be prepared which would have the same osteogenic activity as the P3 OF 31-34 osteogenic preparation isolated according to applicants' methods. Similarly, heterodimers, in which a polypeptide highly homologous to subunit B, such as subunit C, is substituted for subunit B, could also be produced. Pharmaceutically acceptable compositions comprised of such recombinant produced polypeptides in conjunction with physiologically acceptable matrix materials may be prepared and used in the same manner as with polypeptides isolated from human bone.

Numerous modifications and variations in the practice of the invention are expected to occur to those skilled in the art upon consideration of the foregoing descriptions of preferred embodiments thereof. Consequently, only such limitations should be placed upon the invention as appear in the following claims.

We claim:

1. A preparation of an osteogenic protein characterized by comprising a subunit identical or homologous to a subunit in P3 OF 31-34, by a molecular weight of from about 2,5000 to about 38,000 daltons as characterized by non-reducing denaturing gel filtration, and further by the characteristic of eluting at concentrations of between 35% and 45% acetonitrile from a reverse phase high performance liquid chromatography column equilibrated with buffers containing water, acetonitrile and between 0.025% and 0.05% trifluoroacetic acid.

2. The preparation according to claim 1 wherein the osteogenic protein is characterized by a molecular weight of from about 31,000 daltons to about 34,000 daltons as characterized by non-reducing sodium dodecyl sulfate polyacrylamide gel electrophoresis.

3. The preparation according to claim 1 or 2 further characterized by having in its reduced state at least one protein subunit which comigates on reducing sodium dodecyl sulfate polyacrylamide gels with proteins within the molecular weight range of 17,500 to 19,000 or the range of 16,000 to 17,500 daltons.

4. The preparation according to claim 3 wherein one of said subunits is characterized by an amino-terminal sequence selected from the group consisting of
SAPGRRRQQARNRSTPAQDV,
SXKHXXQRXRKKNNN and
STGGKQRSQNRSKTPKNQEA
or is characterized by an internal amino acid sequence selected from the group consisting of
XVVLKNYQDMV,
XEKVVLKNYQDM,
NPEYVPK,
LYLDENEK,
VVEGXGXR,
XATNHAIVQTLVHFIN and
LYLXEYDXVVLXNYQ
wherein X represents an undetermined amino acid.

5. The preparation according to claim 3 wherein the subunits selected from the group characterized by an amino-terminal sequence consisting of:
SAPGRRRQQARNRSTPAQDV and
STGGKQRSQNRSKTPKNQEA
contain aspargaine-linked carbohydrate.

6. The preparation according to claim 1 which is isolated from bovine bone.

7. The preparation according to claim 1 which is isolated from human bone.

8. The preparation according to claim 1 which is isolated from porcine bone.

9. A method for isolating a preparation of an osteogenic protein characterized by comprising a subunit identical or homologous to a subunit in P3 OR 31-34 from demineralized bone tissue, said method comprising:
(a) treating said demineralized bone tissue under aqueous conditions with a solubilizing agent for said osteogenic protein and thereby extracting the osteogenic factor into solution with said solubilizing agent;
(b) subjecting said solution to size fractionation to recover a concentrated pool of proteins of molecular weight between about 10,000 and about 100,000 daltons;
(c) subjecting said concentrated pool to a first chromatography step to recover an active preparation of proteins from a S-Sepharose column equilibrated with 6.0M urea containing 50 mM MES pH 6.5 by eluting the active preparation with 6.0M urea containing 50 mM MES pH 6.5 and 0.5M NaCl;
(d) subjecting the active preparation of step (c) to a buffer exchange step;
(e) subjecting the active preparation of step (d) to a second chromatography step to recover an active preparation of proteins from a Q-Sepharose column equilibrated with 6M urea containing 20 M ethanolamine pH 9.5 by eluting the active preparation with 6.0M urea containing 20 mM ethanolamine pH 9.5 and 0.2M NaCl; and (f) subjecting the active preparation of step (e) to a third chromatography step to recover an active preparation of proteins from a C-18 high performance liquid chromatography column equilibrated with buffers containing trifluoroacetic acid and acetonitrile by eluting the active preparation at concentrations between 35% and 45% acetonitrile.

10. A method for isolating a preparation of on osteogenic protein according to claim 3 further comprising the steps:

(g) subjecting the active fraction of step (f) to a fourth chromatography step to recover an active preparation of proteins from a chelating-Sepharose column charged with Cu2+ and equilibrated with 6M urea containing 50 mM Tris pH 7.5–8.0, 20 mM ethanolamine and 0.5M NaCl by eluting the active preparation with 6M urea containing 50 mM Tris pH 7.4–7.8 and 15 mM imidazole;

(h) subjecting the active fraction of step (g) to a fifth chromatography step to recover an active preparation of proteins from a phenyl-Sepharose column equilibrated with 6M urea containing 50 mM Tris pH 7.4–7.8 and 25% ammonium sulfate by eluting the active preparation with 6M urea containing 50 mM Tris pH 7.4–7.8.

(i) subjecting the active preparation of step (h) to a sixth chromatography step to recover an active preparation of proteins from a C-18 high performance liquid chromatography column equilibrated with buffers containing trifluoroacetic acid and acetonitrile by eluting the active preparation at concentrations between 35% and 45% acetonitrile.

11. A preparation of an osteogenic protein characterized by the capacity of promoting osteogenesis in a mammal and prepared according to the method of claim 9.

12. A preparation of an osteogenic protein characterized by a molecular weight of from about 31,000 to 34,000 daltons as characterized by non-reducing sodium dodecyl sulfate polyacrylamide gel electrophoresis, by the capacity of promoting osteogenesis in a mammal and prepared according to the method of claim 10.

* * * * *